US010018598B2

(12) United States Patent
Oh et al.

(10) Patent No.: US 10,018,598 B2
(45) Date of Patent: Jul. 10, 2018

(54) ULTRASONIC IMAGING APPARATUS AND METHOD OF CONTROLLING THE SAME

(71) Applicant: SAMSUNG ELECTRONICS CO., LTD., Suwon-si (KR)

(72) Inventors: YoungTaek Oh, Seoul (KR); Won-Chul Bang, Seongnam-si (KR); Jiwon Ryu, Suwon-si (KR); Jayeon Jeong, Yongin-si (KR); Minwoo Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 326 days.

(21) Appl. No.: 14/742,033

(22) Filed: Jun. 17, 2015

(65) Prior Publication Data
US 2016/0103221 A1    Apr. 14, 2016

(30) Foreign Application Priority Data

Oct. 13, 2014    (KR) .......................... 10-2014-0137904

(51) Int. Cl.
  *G01S 15/89*    (2006.01)
  *G01N 29/24*    (2006.01)
  *G01S 7/52*     (2006.01)
(52) U.S. Cl.
  CPC .......... *G01N 29/24* (2013.01); *G01S 7/5208* (2013.01); *G01S 7/52073* (2013.01); *G01S 15/8936* (2013.01); *G01S 15/8993* (2013.01); *G01S 15/8995* (2013.01); *G01S 7/52074* (2013.01)

(58) Field of Classification Search
None
See application file for complete search history.

(56) References Cited

U.S. PATENT DOCUMENTS

| 5,078,145 A | * | 1/1992 | Furuhata | A61B 8/14 128/916 |
| 6,500,118 B1 | * | 12/2002 | Hashimoto | A61B 8/00 128/916 |
| 2009/0209859 A1 | * | 8/2009 | Tsujita | A61B 8/00 600/445 |
| 2009/0275833 A1 | * | 11/2009 | Ikeda | A61B 8/0833 600/443 |

(Continued)

*Primary Examiner* — Paul West
*Assistant Examiner* — Mark A Shabman
(74) *Attorney, Agent, or Firm* — Sughrue Mion, PLLC

(57) ABSTRACT

Provided is an ultrasonic imaging apparatus including an ultrasonic probe configured to receive a first ultrasonic signal and a second ultrasonic signal corresponding an object; and an image processor configured to obtain second ultrasonic volume data based on the second ultrasonic signal and relationship information between first information and second information, configured to apply the relationship information to the second ultrasonic volume data and configured to obtain a second ultrasonic cross-sectional image from the second ultrasonic volume data based on the relationship information, where the first information comprises a first position and a first direction corresponding to a position and a direction of the ultrasonic probe receiving the first ultrasonic signal and the second information comprises a second position and a second direction corresponding to a position and a direction of the ultrasonic probe receiving the second ultrasonic signal.

10 Claims, 25 Drawing Sheets

(56) References Cited

U.S. PATENT DOCUMENTS

2010/0239150 A1* 9/2010 Ishikawa ............ A61B 5/0095
  382/131
2014/0219524 A1* 8/2014 Takeguchi ............ A61B 6/463
  382/128

\* cited by examiner

ULTRASONIC IMAGING APPARATUS AND METHOD OF CONTROLLING THE SAME

CROSS-REFERENCE TO RELATED APPLICATION

This application claims priority from Korean Patent Application No. 10-2014-0137904, filed on Oct. 13, 2014 in the Korean Intellectual Property Office, the disclosure of which is incorporated herein by reference in its entirety.

BACKGROUND

1. Field

Apparatuses and methods consistent with exemplary embodiments relate to an ultrasonic imaging apparatus and a method of controlling the same.

2. Description of the Related Art

An imaging apparatus is an apparatus which obtains an external or internal image of an object using visible light, infrared rays, ultrasonic waves, radiation, nuclear magnetic resonance (NMR), or the like. If necessary, the imaging apparatus may control contrast, sharpness, or brightness in the whole or a part of an obtained image, and thus may compensate the obtained image. The imaging apparatus may include a camera, an ultrasonic imaging apparatus, a radiation imaging apparatus, a magnetic resonance imaging apparatus, and so on.

The ultrasonic imaging apparatus is an apparatus which obtains an internal ultrasonic image of a subject, for example, various internal organs or structures of a human body using ultrasonic waves. The ultrasonic imaging apparatus may receive ultrasonic waves reflected by the subject or generated from the subject, and may obtain an ultrasonic image using the received ultrasonic waves. The obtained ultrasonic image may include a tomographic image of the subject, for example, a tomographic image of soft tissue and an image of a blood stream.

The ultrasonic imaging apparatus has a relatively small size and a low price, compared with other imaging apparatuses, and may obtain a three-dimensional image, produce an image in real time, and provide the image to a user. Further, the ultrasonic imaging apparatus is free from a risk of radiation exposure, and thus may be used in various fields such as a medical field and a non-destructive inspection field.

SUMMARY

One or more exemplary embodiments provide an ultrasonic imaging apparatus capable of obtaining the same or similar three-dimensional ultrasonic volumes or ultrasonic images before and after a procedure, and a method of controlling the same.

Also, one or more exemplary embodiments provide an ultrasonic imaging apparatus capable of allowing ultrasonic waves to be irradiated at a position in which an ultrasonic image is obtained before a procedure, and thus obtaining the same or similar three-dimensional ultrasonic volumes or ultrasonic images before and after a procedure, and a method of controlling the same.

Additional aspects of the invention will be set forth in part in the description which follows and in part, will be obvious from the description, or may be learned by practice of the invention.

In accordance with an aspect of an exemplary embodiment, there is provided an ultrasonic imaging apparatus including an ultrasonic probe configured to receive first ultrasonic waves and second ultrasonic waves from a subject, and an image processor configured to obtain relationship information between a first position and a first direction of the ultrasonic probe receiving the first ultrasonic waves and a second position and a second direction of the ultrasonic probe receiving the second ultrasonic waves, to apply the relationship information to second ultrasonic volume data by the second ultrasonic waves, and thus to obtain a second ultrasonic cross-sectional image.

The first position and the second position may be different from each other, or the first direction and the second direction may be different from each other.

The relationship information may include a conversion by which one cross section of first ultrasonic volume data by the first ultrasonic waves coincides with one cross section of the second ultrasonic volume data by the second ultrasonic waves.

The image processor may obtain a first ultrasonic cross-sectional image from first ultrasonic volume data by the first ultrasonic waves, such that the whole or a part of the first ultrasonic cross-sectional image overlaps with the whole or a part of the second ultrasonic cross-sectional image.

The apparatus may further include a displaying part configured to display the first ultrasonic cross-sectional image and the second ultrasonic cross-sectional image in order, in parallel, or to be overlapped with each other.

The image processor may match at least one of the first ultrasonic cross-sectional image and a previously obtained image with the second ultrasonic cross-sectional image.

The previously obtained image may include a radiographic image or a magnetic resonance image.

The apparatus may further include a detector configured to detect a position and a direction of the ultrasonic probe.

The detector may include at least one of an electromagnetic sensor, an optical sensor, a motion sensor, and a first communication module communicating with a second communication module installed at the ultrasonic probe.

The apparatus may further include an output part configured to compute a difference between the first position and the second position, and then to output a signal which induces a change in the position of the ultrasonic probe according to the difference between the first position and second position.

At least one of the first ultrasonic waves and the second ultrasonic waves may be ultrasonic waves received before a procedure, and the other one may be ultrasonic waves received after the procedure.

In accordance with an aspect of another exemplary embodiment, there is provided a method of controlling an ultrasonic imaging apparatus including: receiving first ultrasonic waves from a subject by an ultrasonic probe and obtaining a first position and a first direction of the ultrasonic probe, receiving second ultrasonic waves from the subject by the ultrasonic probe and obtaining a second position and a second direction of the ultrasonic probe, obtaining relationship information between the first position and the first direction and the second position and the second direction, and applying the relationship information to second ultrasonic volume data by the second ultrasonic waves, and obtaining a second ultrasonic cross-sectional image.

The first position and the second position may be different from each other, or the first direction and the second direction may be different from each other.

The relationship information may include a conversion by which one cross section of first ultrasonic volume data by the first ultrasonic waves coincides with one cross section of the second ultrasonic volume data by the second ultrasonic waves.

The method may further include obtaining a first ultrasonic cross-sectional image from first ultrasonic volume data by the first ultrasonic waves, such that the whole or a part of the first ultrasonic cross-sectional image overlaps with the whole or a part of the second ultrasonic cross-sectional image.

The method may further include displaying the first ultrasonic cross-sectional image and the second ultrasonic cross-sectional image in order, in parallel, or to be overlapped with each other.

The method may further include matching at least one of the first ultrasonic cross-sectional image and a previously obtained image with the second ultrasonic cross-sectional image.

The previously obtained image may include a radiographic image or a magnetic resonance image.

The obtaining of the first position and the first direction of the ultrasonic probe and the obtaining of the second position and the second direction of the ultrasonic probe may be performed by a detector configured to detect a position and a direction of the ultrasonic probe.

The detector may include at least one of an electromagnetic sensor, an optical sensor, a motion sensor, and a first communication module communicating with a second communication module installed at the ultrasonic probe.

At least one of the first ultrasonic waves and the second ultrasonic waves may be ultrasonic waves received before a procedure, and the other one may be ultrasonic waves received after the procedure.

The method may further include computing a difference between the first position and the second position, and outputting a signal which induces a change in the position of the ultrasonic probe according to the difference between the first position and the second position.

BRIEF DESCRIPTION OF THE DRAWINGS

The above and/or other aspects of the disclosure will become apparent and more readily appreciated from the following description of the embodiments, taken in conjunction with the accompanying drawings of which.

DETAILED DESCRIPTION

Hereinafter, an ultrasonic imaging apparatus according to one embodiment of the present invention, which irradiates ultrasonic waves inside a subject, receives the ultrasonic waves reflected from a target in the subject, and generates an ultrasonic image based on the received ultrasonic waves, will be described. However, the ultrasonic imaging apparatus is not limited thereto and may include a photoacoustic ultrasonic apparatus using photoacoustic spectroscopy and a Doppler sonography apparatus using Doppler effect, and also may be applied to other various apparatuses which generate an image using the ultrasonic waves.

Hereinafter, the ultrasonic imaging apparatus according to an exemplary embodiment will be described with reference to FIGS. 1 to 20.

Figure 1:
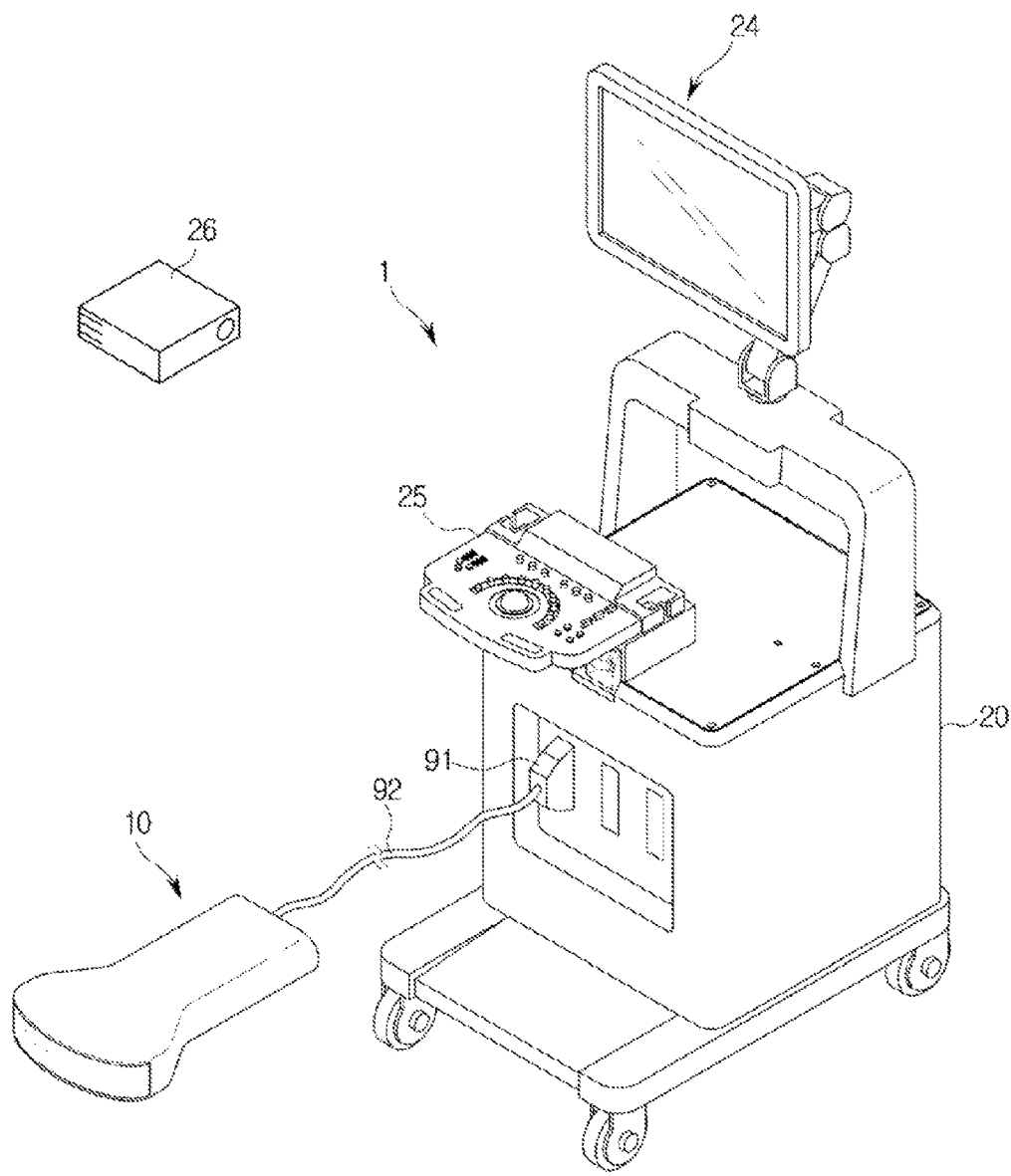
FIG. 1 is a view illustrating an exterior of an ultrasonic imaging apparatus according to an exemplary embodiment.
Figure 2:
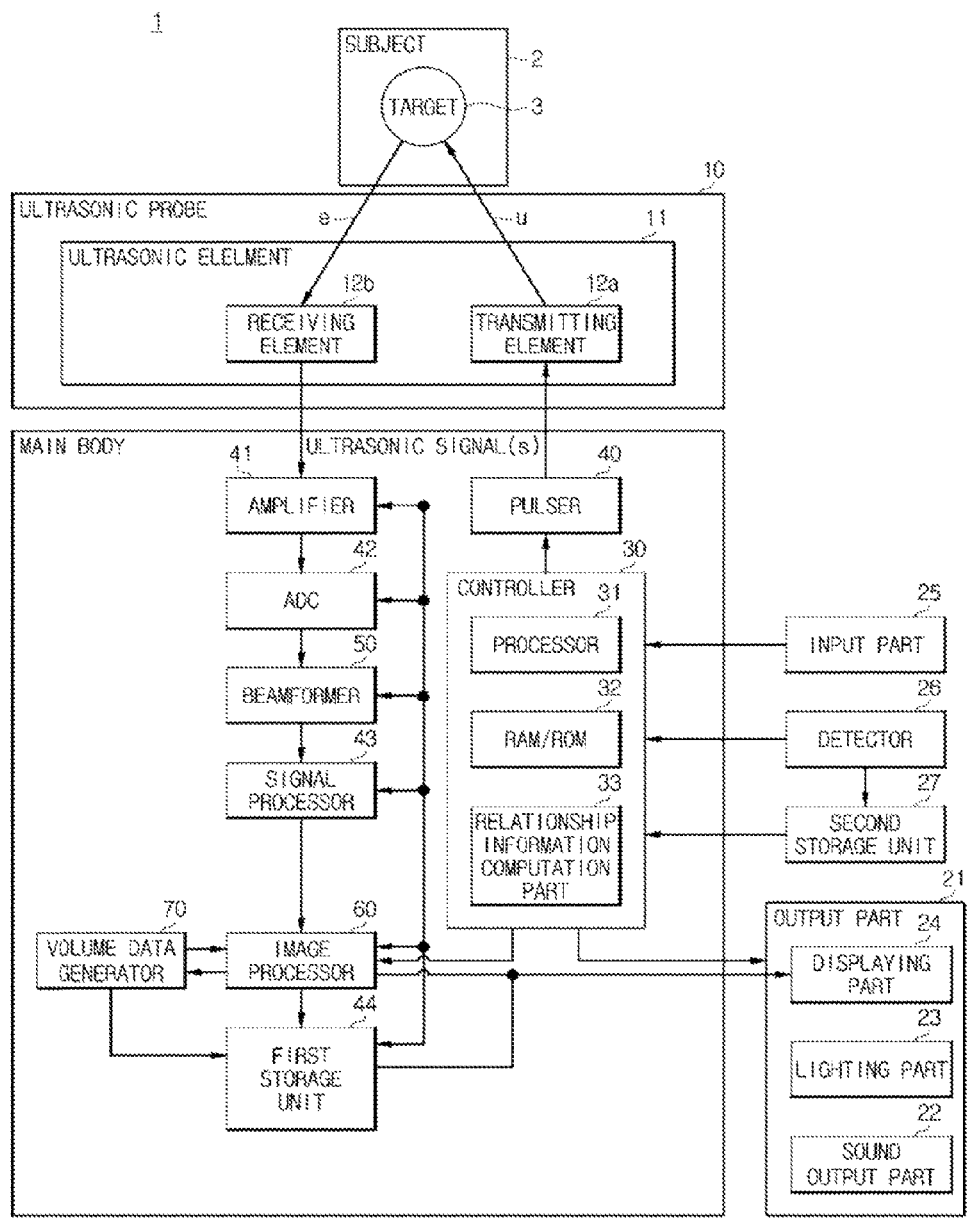
FIG. 2 is a block diagram of the ultrasonic imaging apparatus according to an exemplary embodiment.

FIG. 1 is a view illustrating an exterior of an ultrasonic imaging apparatus according to an exemplary embodiment, and FIG. 2 is a block diagram of the ultrasonic imaging apparatus according to an exemplary embodiment.

As illustrated in FIG. 1, the ultrasonic imaging apparatus 1 according to an exemplary embodiment may include an ultrasonic probe 10 which receives ultrasonic waves irradiated to a target 3 in a subject 2, a main body 20 which produces an ultrasonic image using a signal output from the ultrasonic probe 10 or generates a control signal for controlling the ultrasonic probe 10 or various components installed in the main body 20 according to instructions of a user, and a detector 26 which detects a position of the ultrasonic probe 10.

The subject 2 is an object from which an image of an inner side thereof is taken by the ultrasonic waves, and may include various objects, such as a human body, a fetus, an animal, a machine, and a surface of the earth, from which the image of the inner side thereof may be obtained using the ultrasonic waves.

The target 3 may include an internal material or structure of the subject 2. The target 3 may reflect and irradiate (e) ultrasonic waves (u) irradiated from an outer side or may generate ultrasonic waves by an external stimulus, for example, incident laser.

The user who operates the ultrasonic imaging apparatus 1 and takes an image of the inner side of the subject 2 may include a doctor, a nurse, and an ultrasonic inspector. However, the user is not limited thereto, and any persons who may operate the ultrasonic imaging apparatus 1 may be the user.

According to an exemplary embodiment, the ultrasonic probe 10 and the main body 20 may be connected with each other through a connecting cable 92 so as to transmit an electrical signal output from the ultrasonic probe 10 to the main body 20 or to transmit an electrical signal generated from the main body 20 to the ultrasonic probe 10. According to the exemplary embodiment, a connector 91 coupled to or separated from a port of the main body 20 may be provided at one end of the connecting cable 92. In the same manner, a connector (not shown) coupled to or separated from a port of the ultrasonic probe 10 may be provided at the other end of the connecting cable 92.

According to an exemplary embodiment, the ultrasonic probe 10 and the main body 20 may be connected with each other through a radio communication network so as to transmit the electrical signal output from the ultrasonic probe 10 to the main body 20 or to transmit the electrical signal generated from the main body 20 to the ultrasonic probe 10. In this case, a wireless communication module including an antenna and a wireless communication chip may be installed in the ultrasonic probe 10 and the main body 20, respectively. The wireless communication module may be a short range wireless communication module using at least one of Bluetooth, Bluetooth low energy, infrared data association (IrDA), Wi-Fi, Wi-Fi direct, ultra wideband (UWB), and near field communication (NFC), or may be a wireless communication module supporting a wireless LAN standard (IEEE802.11x) of the Institute of Electrical and Electronics Engineers.

The ultrasonic probe 10 may receive the ultrasonic waves (e) generated from the target 3 in the subject 2. According to the exemplary embodiment, the ultrasonic probe 10 may generate the ultrasonic waves (u) and then transmit the generated ultrasonic waves (u) to the target 3 in the subject 2.

Referring to FIG. 2, the ultrasonic probe 10 may include an ultrasonic element 11 which receives the ultrasonic waves (e) and transmits an ultrasonic signal (s) as the electrical signal corresponding to the received ultrasonic waves (e). The ultrasonic element 11 may generate and irradiate the ultrasonic waves (u). A plurality of ultrasonic elements 11 may be provided at the ultrasonic probe 10. According to an exemplary embodiment, as illustrated in FIG. 2, the ultrasonic element 11 may include a transmitting element 12a which generates the ultrasonic waves (u) having a predetermined frequency through a pulser 40 in the main body 20, and a receiving element 12b which receives the ultrasonic waves (e) generated from the inner side of the subject 2. According to an exemplary embodiment, the ultrasonic element 11 may include a transmitting/receiving element (not shown) which may perform both of the generation of the ultrasonic waves (u) and the receiving of the ultrasonic waves (e) transmitted from the target 3. According to still an exemplary embodiment, the ultrasonic element 11 may include all of the transmitting element 12a, the receiving element 12b, and the transmitting/receiving element. The ultrasonic element 11 may be realized by an ultrasonic transducer.

Figure 3:
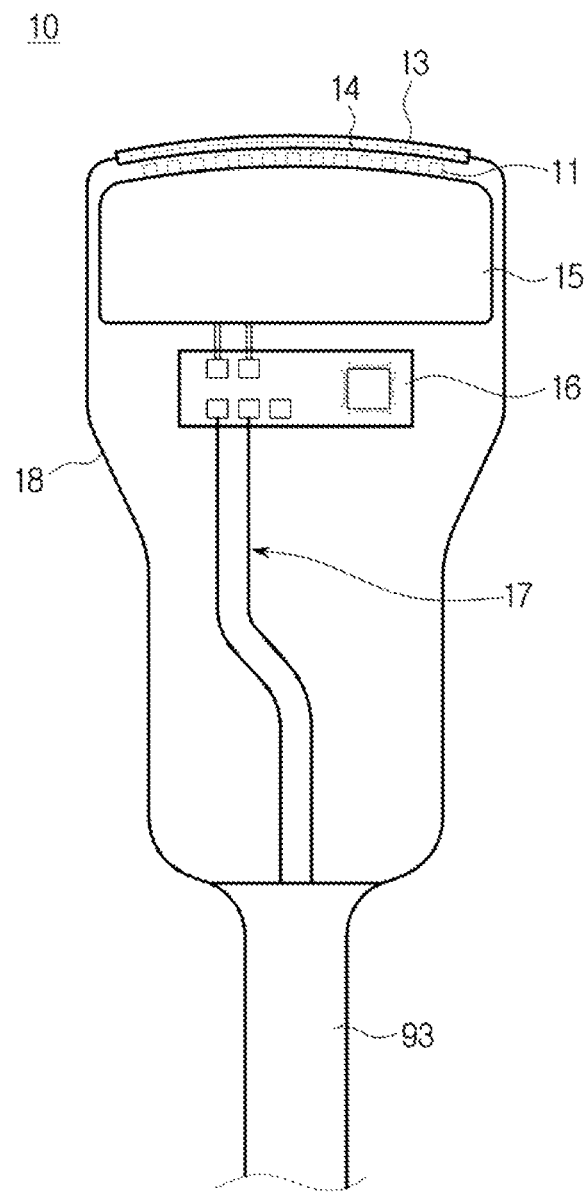
FIG. 3 is a block diagram of an ultrasonic probe according to an exemplary embodiment.

Hereinafter, the ultrasonic probe 10 will be described in detail with reference to FIG. 3. FIG. 3 is a block diagram of an ultrasonic probe according to an exemplary embodiment of the present invention.

Referring to FIG. 3, the ultrasonic probe 10 may include an acoustic lens 13, an acoustic matching layer 14, the ultrasonic element 11, an ultrasonic element supporter 15, an ultrasonic probe processor 16, a connecting wire 17, and a housing 18 which accommodates these components therein.

The acoustic lens 13 may focus or diverge sonic waves or ultrasonic waves passing through the acoustic lens 13. According to an exemplary embodiment, the acoustic lens 13 may refract the ultrasonic waves (u) passing through the acoustic lens 13 so that the ultrasonic waves (u) generated from the ultrasonic element 11 is focused on the target 3. The acoustic lens 13 may have a curved shape to focus or diverge the sonic waves or the ultrasonic waves. The acoustic lens 13 may be formed of various materials, such as glass and a synthetic resin, which would be considered by a person skilled in the art.

The acoustic matching layer 14 may maintain a feature of straightness of the ultrasonic waves generated from the ultrasonic element 11, and a property and an intensity of the ultrasonic waves, or may minimize reflection of the ultrasonic waves by other media. The acoustic matching layer 14 may be installed adjacent to the acoustic lens 13. The acoustic matching layer 14 may be formed in a film shape. The acoustic matching layer 14 may be formed of various materials, such as a metal powder, ceramic powder, and silicon wafer, which would be considered by a person skilled in the art.

The ultrasonic element 11 may convert an electrical signal having a predetermined frequency into mechanical vibration having the same frequency and may generate ultrasonic waves having a frequency corresponding to that of the electrical signal. Specifically, when a voltage generated from the pulser 40 is applied to the ultrasonic element 11, a piezoelectric resonator or a thin film of the ultrasonic element 11 is vibrated, and the ultrasonic waves are generated according to the vibration of the piezoelectric resonator or the thin film. Therefore, the ultrasonic element 11 may generate the ultrasonic waves. As described above, the ultrasonic waves generated by the ultrasonic element 11 may be irradiated to the inner side of the subject 2 and focused on the target 3 in the subject 2. The irradiated ultrasonic waves may be focused on one target 3 (single focusing) or a plurality of targets 3 (multi-focusing).

Also, the ultrasonic element 11 may receive the ultrasonic waves and may output the ultrasonic signal (s), while vibrating at a frequency corresponding to that of the received ultrasonic waves. Because one ultrasonic element 11 may output a signal of one channel, a plurality of ultrasonic elements 11 may output signals of a plurality of channels. The output ultrasonic signal (s) may be transmitted to an amplifier 41 or a beamformer 50.

The ultrasonic element 11 may be realized using the ultrasonic transducer. The ultrasonic transducer may include a piezoelectric ultrasonic transducer using a piezoelectric effect of a piezoelectric substance, a magnetostrictive ultrasonic transducer using a magnetostrictive effect of a magnetic substance, and a capacitive micro-machined ultrasonic transducer using vibration of a few hundred or thousand micro-machined thin films. Also, the ultrasonic element 11 may include various other kinds of transducers which generate the ultrasonic waves according to the electrical signal or generate the electrical signal according to the ultrasonic waves.

Figure 4:
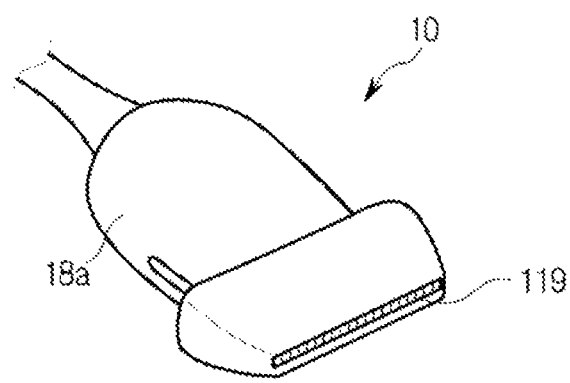
FIG. 4 is a view illustrating an exterior of the ultrasonic probe in which a transducer is arranged in a one-dimensional array.
Figure 5:
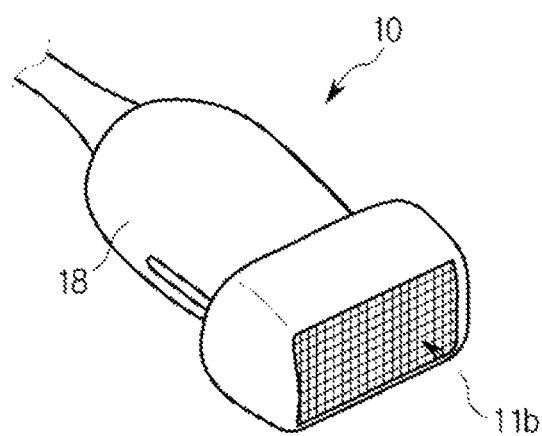
FIG. 5 is a view illustrating the exterior of the ultrasonic probe in which the transducer is arranged in a two-dimensional array.

FIG. 4 is a view illustrating an exterior of the ultrasonic probe in which the transducer is arranged in a one-dimensional array, and FIG. 5 is a view illustrating the exterior of the ultrasonic probe in which the transducer is arranged in a two-dimensional array.

The ultrasonic element 11 may be arranged in various types. For example, as illustrated in FIG. 4, ultrasonic elements 11a may be arranged in a one-dimensional array. In this case, as illustrated in FIG. 4, the ultrasonic elements 11a may be linearly arranged, or may be arranged in a curved shape in which an ultrasonic element disposed at a center or therearound protrude more outward than other ultrasonic elements, or is recessed in the opposite direction. Hereinafter, the term "outward" means a direction in which the subject 2 is located, and the "opposite direction" means a direction which is opposite to a position of the subject 2 based on the ultrasonic element 11. When the ultrasonic elements 11 are arranged in the curved shape, as described above, the ultrasonic element 11 irradiates an ultrasonic beam in the form of a fan shape, and thus an ultrasonic image may have the fan shape. Further, as illustrated in FIG. 5, the ultrasonic elements 11b may be arranged in a two-dimensional array having a plurality of lines. When the ultrasonic elements 11b are arranged in the two-dimensional array, it is possible to maintain a high resolution in a vertical direction. When the ultrasonic elements 11b are arranged in the two-dimensional array, a three-dimensional image may be obtained with respect to the inner side of the subject 2.

In addition, the ultrasonic elements 11 may be arranged in various types, such as a circular shape and an elliptical shape, which would be considered by a person skilled in the art.

The ultrasonic elements 11 may be installed at a front surface of the ultrasonic element supporter 15. Here, the front surface of the ultrasonic element supporter 15 means one surface in a direction of the subject 2. Further, a side surface or a rear surface of the ultrasonic element supporter 15 may be defined based on the front surface of the ultrasonic element supporter 15. The ultrasonic elements 11 may be installed at the ultrasonic element supporter 15 in various forms. In the case of the ultrasonic probe having the one-dimensional array, the ultrasonic elements 11 may be installed at the ultrasonic element supporter 15 in a line. In the case of the ultrasonic probe having the two-dimensional array, the ultrasonic elements 11 may be installed at the ultrasonic element supporter 15 in a plurality of lines.

The ultrasonic element supporter 15 may support the ultrasonic elements 11, and at the same time, may absorb some of the ultrasonic waves generated from the ultrasonic elements 11, which are irradiated in the opposite direction, or may radiate heat generated while the ultrasonic elements 11 are operated. The ultrasonic element supporter 15 may include an acoustic absorption material which absorbs the ultrasonic waves, and a heat transfer material which assists the heat emission. The acoustic absorption material may be formed of an epoxy resin or a hafnium oxide, such as hafnium oxide metal powder, which may absorb the sonic waves or the ultrasonic waves. The heat transfer material may be formed of an aluminum oxide such as graphite, tungsten, a tungsten oxide, silicon, and alumina, or a material having thermal conductivity, such as a glass micro balloon filter.

The ultrasonic probe processor 16 or a substrate 16a on which the ultrasonic probe processor 16 is mounted may be provided at the rear surface or the side surface of the ultrasonic element supporter 15. The ultrasonic probe processor 16 may perform a basic process with respect to the ultrasonic signal (s) transmitted from the ultrasonic element 11, which amplifies the ultrasonic signal (s) or converts the ultrasonic signal (s) into a digital signal. According to an exemplary embodiment, the ultrasonic probe processor 16 may also perform a function of the beamformer 50. Further, if necessary, the ultrasonic probe processor 16 may generate a control signal which controls an entire operation of the ultrasonic probe 10. The ultrasonic probe processor 16 may be realized by various semiconductor chips and relevant components. FIG. 3 illustrates an example in which the ultrasonic probe processor 16 and the substrate 16a are installed at the rear surface of the ultrasonic element supporter 15. However, positions thereof are not limited thereto, and the ultrasonic probe processor 16 and the substrate 16a may be installed at any positions in the housing 18 of the ultrasonic probe 10 according to a designer's selections.

According to the exemplary embodiment, a vibrator (not shown) may be installed at the ultrasonic probe 10. The vibrator may be vibrated by a control signal of a controller 30, while vibrating the ultrasonic probe 10, and thus may inform the user grasping the ultrasonic probe 10 of a variety of information such as incorrectness of a position or a direction.

According to the exemplary embodiment, an electromagnetic sensor (EM sensor) may be installed at the ultrasonic probe 10. The EM sensor may detect an electromagnetic field and may obtain information on a position and/or a direction of the ultrasonic probe 10. The EM sensor may be installed on the above-mentioned substrate 16a or at an exterior housing 18.

According to the exemplary embodiment, a motion sensor which detects movement of the ultrasonic probe 10 may be installed at the ultrasonic probe 10. The motion sensor may include an acceleration sensor. The motion sensor may be installed on the above-mentioned substrate 16a or at the exterior housing 18.

The exterior housing 18 may accommodate various components and may also include a handle which is grasped by the user. The exterior housing 18 may have various types of probes according to kinds of the subject 2 or the target 3. For example, the exterior housing 18 may have different shapes according to the ultrasonic imaging apparatuses such as an abdominal ultrasonic imaging apparatus, an endovaginal ultrasonic imaging apparatus, an anal ultrasonic imaging apparatus, and a renal ultrasonic imaging apparatus. The ultrasonic element 11 may be installed at one end of the exterior housing 18. A connecting wire 93 may be coupled to other end thereof according to the exemplary embodiment.

The connecting wire 93 may serve as a passage which transmits the ultrasonic signal (s) or a beamformed ultrasonic signal to the main body 20. The connecting wire 93 may form a part of the connecting cable 92. The ultrasonic signal (s) or the beamformed ultrasonic signal may be transmitted to the main body 20 through the connecting wire 93, the connecting cable 92, the connector 91 and a slot. When the wireless communication module is installed at the ultrasonic probe 10, the connecting wire 93 may be omitted.

The user may grasp the exterior housing 18 of the ultrasonic probe 10, may direct the surface, on which the ultrasonic elements 11 are installed, in the direction of the subject 2, such that the ultrasonic probe 10 irradiates the ultrasonic waves (u) on the target 3 in the subject 2, and/or receives the ultrasonic waves (e) generated or reflected from the target 3 in the subject 2, and thus may perform ultrasonography.

Hereinafter, it is assumed that the ultrasonic waves received by the ultrasonic probe 10 are called "first ultrasonic waves", and an image or ultrasonic volume data obtained based on the first ultrasonic waves is called a "first image" or "first ultrasonic volume data". Also, it is assumed that the ultrasonic waves received by the ultrasonic probe 10 after time passed are called "second ultrasonic waves", and an image or ultrasonic volume data obtained based on the second ultrasonic waves is called a "second image" or "second ultrasonic volume data". The elapsed time means a period of time in which the position and/or the direction of the ultrasonic probe 10 at a second photographing operation may be different from the position and/or the direction of the ultrasonic probe 10 at a first photographing operation. The elapsed time may include both of a short period of time during a short break or the like and a long period of time required to perform a medical procedure or the like. For example, the first ultrasonic waves may be the ultrasonic waves obtained before the medical procedure, and the second ultrasonic waves may be the ultrasonic waves obtained after the medical procedure.

As described above, the definitions of the first ultrasonic waves, the second ultrasonic waves, the first image, the second image, the first ultrasonic volume data, and the second ultrasonic volume data serve to avoid the complexity of description. If necessary, the first ultrasonic waves, the second ultrasonic waves, the first image, the second image, the first ultrasonic volume data, and the second ultrasonic volume data may be defined regardless of their order, and thus may not be construed as an ordinal sequence according to the designated ordinal numbers.

Figure 6:
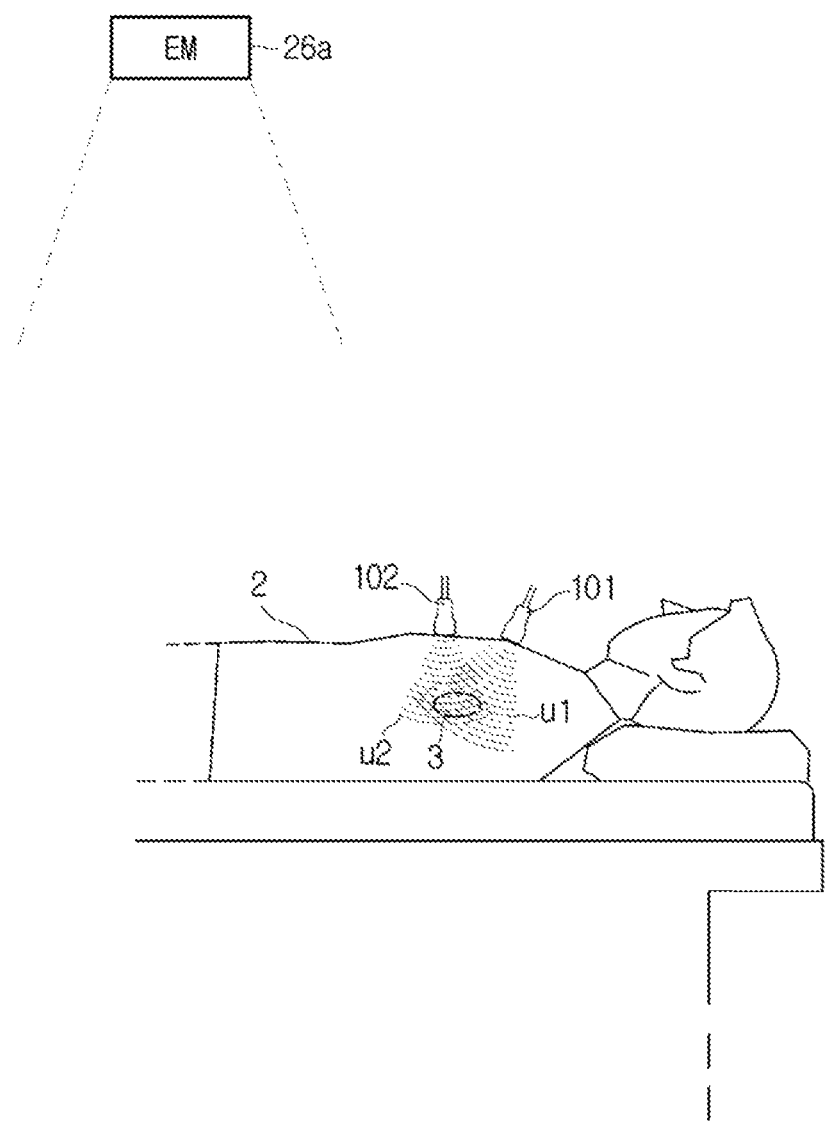
FIG. 6 is a view for describing a position and a direction of the ultrasonic probe.

FIG. 6 is a view for describing the position and the direction of the ultrasonic probe.

As illustrated in FIG. 6, the user may perform a photographing operation with respect to the same target 3 in the same subject 2 a plurality of times using ultrasonic probes 101 and 102. Herein, the photographing operation previously performed is called a first photographing operation, and another photographing operation performed after the first photographing operation is called a second photographing operation. The first and second photographing operations may be performed using the same ultrasonic probe or ultrasonic imaging apparatus, or may be performed using different ultrasonic probes or ultrasonic imaging apparatuses. The first and second photographing operations are separately expressed to indicate an order of the photographing operations. Therefore, it is not interpreted only that the first photographing operation is a photographing operation which is first performed, and the second photographing operation is a photographing operation which is performed after the first photographing operation.

It is difficult for the user to completely coincide the position and/or the direction of the ultrasonic probe 101 at the first photographing operation with the position and/or the direction of the ultrasonic probe 102 at the second photographing operation. When a time difference between the first and second photographing operations is large due to the procedure or the like, it is further difficult to coincide the positions and/or the directions of the ultrasonic probes 101 and 102 at both of the photographing operations with each other. Therefore, when a plurality of photographing operations are performed using the ultrasonic probes 101 and 102, at least one of the position and the direction may not coincide, as illustrated in FIGS. 7 to 9.

Figure 7:
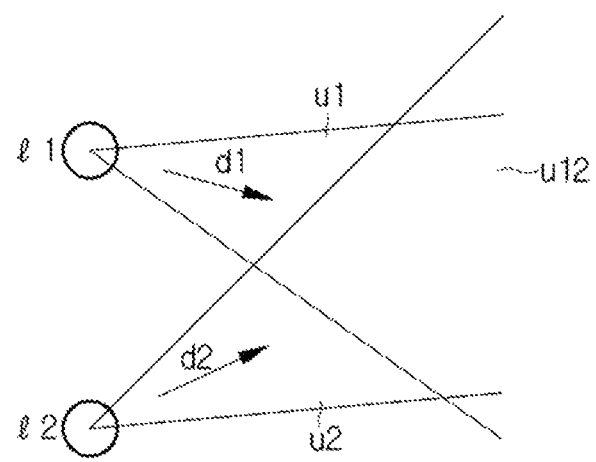
FIGS. 7 to 9 are views for describing the ultrasonic probe which irradiates and receives ultrasonic waves to/from various positions and in various directions.
Figure 8:
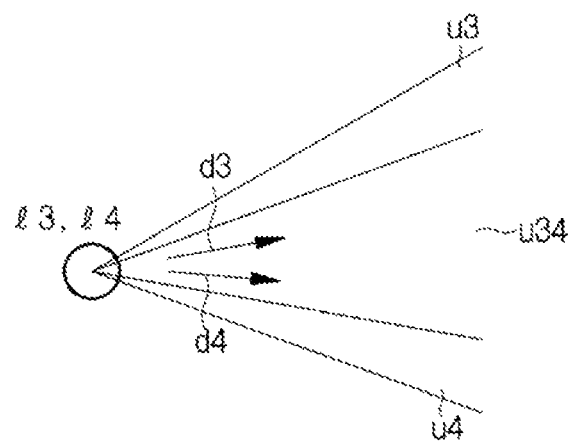
Figure 9:
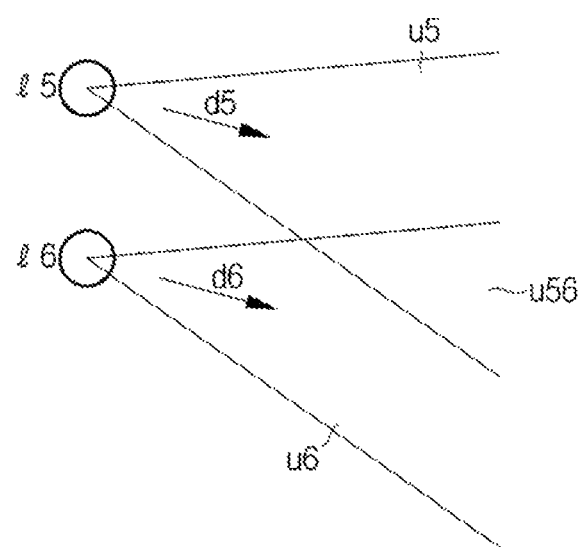

FIGS. 7 to 9 are views for describing the ultrasonic probe which receives the ultrasonic waves at different times, respectively. FIGS. 7 to 9 do not separately illustrate the ultrasonic probe 10. However, the ultrasonic probe 10 may be disposed at each of irradiation positions I1 to I6 illustrated in FIGS. 7 to 9 so as to irradiate the ultrasonic waves u1 to u6 and then to receive the ultrasonic waves reflected from the target 3. Further, the ultrasonic probe 10 may irradiate the ultrasonic waves u1 to u6 in irradiation directions d1 to d6.

According to FIG. 7, the position I1 and/or the direction d1 of the ultrasonic probe 101 at the first photographing operation may be different from the position I2 and/or the direction d2 of the ultrasonic probe 102 at the second photographing operation, respectively. In this case, because both of the ultrasonic waves u1 at the first photographing operation and the ultrasonic waves u2 at the second photographing operation are irradiated in the formed of the fan shape, an overlapping area u12 through which both of the ultrasonic waves u1 and u2 pass may exist at the inner side of the subject 2.

According to FIG. 8, the position I3 of the ultrasonic probe 101 at the first photographing operation and the position I4 of the ultrasonic probe 102 at the second photographing operation may be the same as or adjacent to each other, but the direction d3 at the first photographing operation and the direction d4 at the second photographing operation may be different from each other. Also in this case, as described above, because both of the ultrasonic waves u3 at the first photographing operation and the ultrasonic waves u4 at the second photographing operation are irradiated in the formed of the fan shape, an overlapping area u34 through which both of the ultrasonic waves u3 and u4 pass may exist at the inner side of the subject 2.

According to FIG. 9, the direction d5 of the ultrasonic probe 101 at the first photographing operation and the direction d6 of the ultrasonic probe 102 at the second photographing operation may be the same as or similar to each other, but the position I5 at the first photographing operation and the position I6 at the second photographing operation may be different from each other. As described above, an overlapping area u56 through which both of the ultrasonic waves u5 and u6 pass may exist at the inner side of the subject 2.

As illustrated in FIGS. 7 to 9, when the positions and/or the directions of the ultrasonic probes 101 and 102 are different from each other, respectively, the irradiation position and/or the irradiation direction of the irradiated ultrasonic waves u1 and u2 are also different from each other, respectively. Therefore, the ultrasonic images or the three-dimensional volume data, which are different from each other, respectively, may be obtained at the first and second photographing operations.

Referring to FIG. 2, the ultrasonic signal may be transmitted to the main body 20. As described above, the ultrasonic signal may be transmitted from the ultrasonic probe 10 to the main body 20 using a wired communication technique or a wireless communication technique.

Referring to FIG. 2, the main body 20 may include the controller 30, the pulser 40, the amplifier 41, an analog-to-digital converter 42, the beamformer 50, a signal processor 43, a first storage unit 44, an image processor 60 and a volume data generator 70. If necessary, some of them may be omitted. Also, some of them may be provided at the ultrasonic probe 10, or may be provided at a separate workstation (not shown) connected with the main body 20 through a wired and wireless communication network.

The controller 30, the pulser 40, the amplifier 41, the analog-to-digital converter 42, the beamformer 50, the signal processor 43, the image processor 60, and the volume data generator 70 may be realized by a processor provided at the ultrasonic probe 10, the main body 20, or the workstation, for example, at least one of a central processing unit (CPU) and a graphic processing unit (GPU). The CPU and the GPU may use various semiconductor chips and a printed circuit board on which the semiconductor chips are mounted.

The first storage unit 44 may be realized by a semiconductor memory unit, a magnetic disc memory unit, or an optical disc memory unit installed at the main body 20, an inner side of the workstation, or an outside. Meanwhile, when the control signal or data is transmitted from one of the construction elements 30 to 70 provided at the main body 20 to the other one, the control signal or data may be temporarily or non-temporarily stored in a predetermined memory unit for convenience in a computing process. Here, the predetermined memory unit may include a volatile memory unit and a non-volatile memory unit.

The controller 30 may control an entire operation of the ultrasonic imaging apparatus M according to the user's command or a previously defined set. Here, the user's command may be input through an input part 25. The previously defined set may be stored in the first storage unit 44. For example, the control signal may be transmitted to the vibrator provided at the ultrasonic probe 10 so as to control the ultrasonic probe 10, may control a light to be turned on, or may control a sound output part 22 to output a predetermined sound. Further the controller 30 may control the pulser 40 to control the ultrasonic probe 10. Specifically, the controller 30 may generate a control signal corresponding to a frequency of the ultrasonic waves to be irradiated, and then may transmit the generated control signal to the pulser 40. The control signal may include information on a frequency or level of a voltage applied to an ultrasonic irradiator 111.

According to an exemplary embodiment, the controller 30 may include a processor 31, a RAM or ROM 32, and a relationship information computation part 33.

The processor 31 may perform various necessary computations and may generate a control signal which controls the ultrasonic probe 10 and the main body 20. The processor 31 may be programmed with a predetermined algorithm so as to perform the various computing and controlling operations. The processor 31 may be realized by one or more semiconductor chip and relevant components thereof.

The RAM or ROM 32 may temporarily or semi-permanently store a program related to the processor 31, or may temporarily or non-temporarily store data transmitted from the input part 25, the detector 26, or a second storage unit 27 so as to assist an operation of the processor 31.

The controller 30 may include the relationship information computation part 33 which computes relationship information based on data about at least one of the position and the direction of the ultrasonic probe 10 transmitted from the detector 26 or the second storage unit 27. The relationship information may mean a relationship between a first position and direction of the ultrasonic probe 101 receiving the first ultrasonic waves and a second position and direction of the ultrasonic probe 102 receiving the second ultrasonic waves. More specifically, the relationship information may include a conversion T for coinciding one cross section of the first ultrasonic volume data obtained based on the first ultrasonic waves previously received and one cross section of the second ultrasonic volume data obtained based on the second ultrasonic waves received later.

The conversion T may be computed by the following Equation 1:

$$T = K_1^{-1} K_2 \qquad \text{[Equation 1]}$$

Here, T is the conversion, K1 is a value related to the ultrasonic probe 101 receiving the first ultrasonic waves, and K2 is a value related to the ultrasonic probe 102 receiving the second ultrasonic waves. The value related to the ultrasonic probe 101 receiving the first ultrasonic waves may include at least one of the first position and the first direction. Specifically, K1 may be obtained by combining two-dimensional or three-dimensional coordinates indicating the first position and two-dimensional or three-dimensional vector components indicating the first direction. The value related to the ultrasonic probe 102 receiving the second ultrasonic waves may include at least one of the second position and the second direction. In the same manner as described above, K2 may be the conversion obtained by combining two-dimensional or three-dimensional coordinates indicating the second position and two-dimensional or three-dimensional vector components indicating the second direction. The conversion T obtained using the value K1 related to the ultrasonic probe 101 receiving the first ultrasonic waves and the value K2 related to the ultrasonic probe 102 receiving the second ultrasonic waves may be expressed mathematically in the form of a matrix. In this case, the matrix may be a 4×4 matrix or a 6×6 matrix according to the dimension of the coordinates and the vectors. In addition, the conversion may be expressed in various types.

The relationship information computation part 33 may compute the conversion T using the above-mentioned Equation 1 and thus may obtain the relationship information.

The relationship information computation part 33 may be realized by the processor 31, or may be realized by a processor which is provided separately from the processor 31, as illustrated in FIG. 2. The relationship information computation part 33 may be realized by a semiconductor chip and relevant components, and the semiconductor chip may be installed on a printed circuit board.

The pulser 40 may generate a voltage which drives the ultrasonic element 11 of the ultrasonic probe 10. The pulser 40 may generate the voltage having a predetermined amplitude and a predetermined frequency according to the control signal received from the controller 30. The ultrasonic element 11 may be vibrated according to the amplitude and the frequency of the voltage output from the pulser 40 to generate the ultrasonic waves. A frequency and an intensity of the ultrasonic waves generated from the ultrasonic element 11 may be dependent on the amplitude and the frequency of the voltage generated from the pulser 40. The voltage output from the pulser 40 may be applied to the ultrasonic element 11 so as to have a predetermined time difference, and thus the ultrasonic waves generated from the ultrasonic element 11 and irradiated on the subject 2 may be focused on a predetermined position or steered in a predetermined direction.

The amplifier 41 may amplify the ultrasonic signal of one or two or more channels. A gain of the amplifier 41 may be arbitrarily determined by a system designer or a user of a beamforming device. The amplifier 41 may be provided at the ultrasonic probe 10 according to the exemplary embodiment. Further, if necessary, the amplifier 41 may be omitted. The amplifier 41 may amplify differently the ultrasonic signals of the plurality of channels output from the plurality of ultrasonic elements 11 according to the exemplary embodiment. Therefore, the amplifier 41 may compensate a difference in intensity between the ultrasonic signal of the plurality of channels due to a depth of the target 3 or the like. The amplifier 41 may transmit the amplified ultrasonic signal to the analog-to-digital converter 42 or the beamformer 50.

The analog-to-digital converter 42 may convert the ultrasonic signal from an analog signal to a digital signal and then may transmit the converted signal to the beamformer 50. The analog-to-digital converter 42 may perform a sampling from the ultrasonic signal as the analog signal according to a predetermined sampling rate, and then may output the digital signal. According to the exemplary embodiment, the analog-to-digital converter 42 may be omitted.

Figure 10:
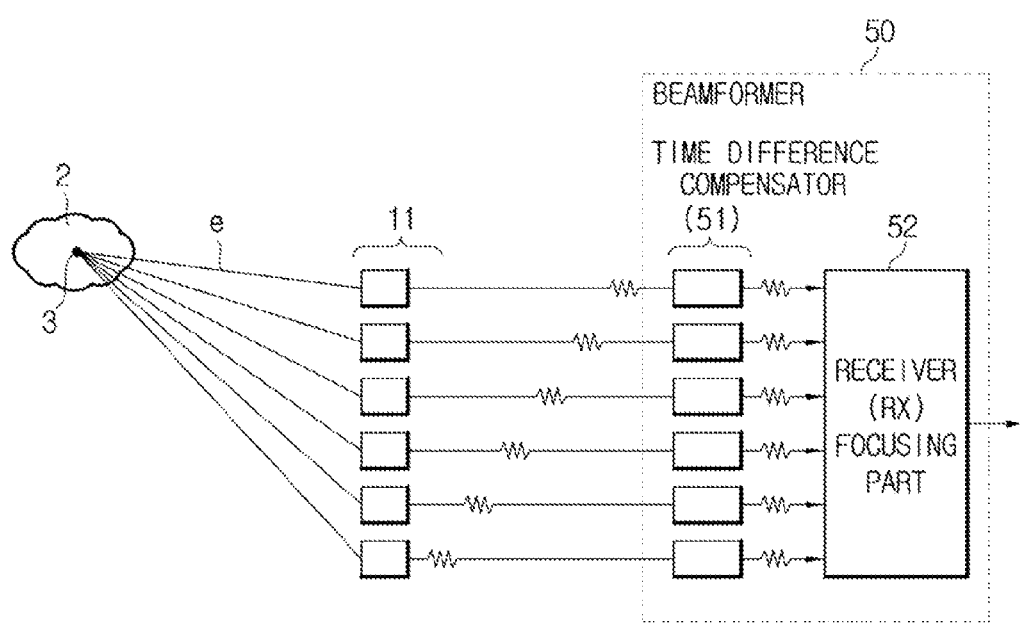
FIG. 10 is a view for describing a beamformer of the ultrasonic imaging apparatus.

FIG. 10 is a view for describing the beamformer of the ultrasonic imaging apparatus.

The beamformer 50 may focus the signal transmitted from the ultrasonic element 11, the amplifier 41, or the analog-to-digital converter 42, and may produce a beamformed signal. The beamformer 50 may perform functions of electronic beam scanning, steering, focusing, apodizing, and adjusting an aperture of the signals of the plurality of channels. The beamformer 50 may be realized by one or two or more semiconductor chips and a printed circuit board on which the semiconductor chips are mounted, or may be realized by various devices which would be considered by a person skilled in the art.

According to an exemplary embodiment, as illustrated in FIG. 10, the beamformer 50 may include a time difference compensator 51 and a receiver focusing part 52. The time difference compensator 51 may compensate the time difference between the ultrasonic signals of the plurality of channels. The ultrasonic waves (e) transmitted from the target 3 in the subject 2 may be transmitted to the plurality of ultrasonic elements 11, and the plurality of ultrasonic elements 11 may output the signals of the plurality of channels. In this case, the time difference between the signals of the plurality of channels may occur according to a distance between the target 3 and each ultrasonic element 11 or properties of the ultrasonic element 11. The time difference compensator 51 may delay transmitting of some of the signals of the plurality of channels, and thus may compensate the time difference between the signals of the plurality of channels. The receiver focusing part 52 may synthesize the ultrasonic signals of the plurality of channels, in which the time difference is compensated, and may produce the beamformed signal. The receiver focusing part 52 may apply a predetermined weighted value to the ultrasonic signal of each channel and thus synthesize the ultrasonic signals of the plurality of channels. The predetermined weighted value may be determined regardless of the ultrasonic signal, or may be determined according to the ultrasonic signal. The beamformed signal may be transmitted to the signal processor 43.

The signal processor 43 may perform various signal processing operations with respect to the beamformed signal. For example, the signal processor 43 may perform at least one of a filtering process, a detecting process, and a compressing process. The filtering process may mean a process which removes other signals except a signal having a certain bandwidth by applying a filter to the beamformed signal. The filtering process may include a harmonic imaging process which removes a basic frequency component and passes a harmonic signal. The detecting process may mean a process which converts a voltage of the ultrasonic signal from a radio frequency type to a video frequency type. The compressing process may mean a process which reduces a difference in the amplitude between the ultrasonic signals. The signal processor 43 may be omitted, if necessary.

The image processor 60 may convert the beamformed signal or the signal processed from the signal processor 43 into an image type. The image processor 60 may produce an ultrasonic image using a scan conversion. The produced ultrasonic image may include an A mode, B mode, or M mode ultrasonic image. The A mode ultrasonic image means an ultrasonic image in which a reflection intensity is imaged with an amplitude based on a distance or a time between the target 3 and the ultrasonic probe 10. The B mode ultrasonic image means an ultrasonic image in which an intensity of the ultrasonic waves is expressed using brightness. The M mode ultrasonic image means an ultrasonic image in which a change in a motion of the subject is imaged. The ultrasonic image may include a Doppler image using the Doppler effect.

The image processor 60 may compensate the ultrasonic image. For example, the image processor 60 may compensate brightness, luminance, sharpness, contrast, or color in the whole or a part of the ultrasonic image. The image processor 60 may remove noise or may perform a pixel interpolation.

Further, the image processor 60 may generate other images based on the obtained ultrasonic image.

For example, the image processor 60 may combine a plurality of images in parallel and may generate a panoramic image.

Also, the image processor 60 may match and synthesize the plurality of images and may produce a synthesized image. Here, the matched images may include a first ultrasonic cross-sectional image obtained from the first ultrasonic volume data or a second ultrasonic cross-sectional image obtained from the second ultrasonic volume data. In addition, the matched images may include images obtained by other imaging apparatus such as a magnetic resonance imaging (MRI) apparatus and a computed tomography (CT) apparatus.

Also, the image processor 60 may overlap the plurality of images and may process an overlapped image. The image processing operations of the image processor 60 as described above may be performed according to the user's instruction or a previously defined set. In the producing of the overlapped image, the image processor 60 may produce the overlapped image by applying the same transparency to both of a first ultrasonic cross-sectional image P1 and a second ultrasonic cross-sectional image P2 obtained using the conversion T, or may produce the overlapped image by applying different transparency to both of them.

The image processor 60 may obtain the ultrasonic volume data generated from the volume data generator 70 and may perform various image processing operations using the obtained ultrasonic volume data. For example, the image processor 60 may obtain the ultrasonic cross-sectional image from the ultrasonic volume data.

For example, the image processor 60 may obtain the relationship information from the controller 30, specifically the relationship information computation part 33. Here, the relationship information may mean information on the relationship between the first position and/or the first direction of the ultrasonic probe receiving the first ultrasonic waves and the second position and/or the second direction of the ultrasonic probe receiving the second ultrasonic waves, and may include the conversion computed using the first position and/or the first direction and the second position and/or the second direction. In this case, the relationship information may coincide one cross section of the first ultrasonic volume data by the first ultrasonic waves with one cross section of the second ultrasonic volume data by the second ultrasonic waves.

Then, the image processor 60 may apply the obtained relationship information to the first ultrasonic volume data by the first ultrasonic waves and may obtain the first ultrasonic cross-sectional image. Or the image processor 60 may apply the obtained relationship information to the second ultrasonic volume data by the second ultrasonic waves and may obtain the second ultrasonic cross-sectional image. This will be described later.

The image processor 60 may transmit or store the generated or compensated ultrasonic image or the various obtained images to the first storage unit 44, or may display the generated or compensated ultrasonic image or the various obtained images through a displaying part 24 of an output part 21. Further, the image processor 60 may transmit the generated or compensated ultrasonic image to the volume data generator 70 to obtain the ultrasonic volume data.

The image processor 60 may be realized by the CPU or the GPU which may be realized by one or more semiconductor chips built in the main body 20. According to the exemplary embodiment, the image processor 60 may be realized by the processor 31 of the controller 30.

Figure 11:
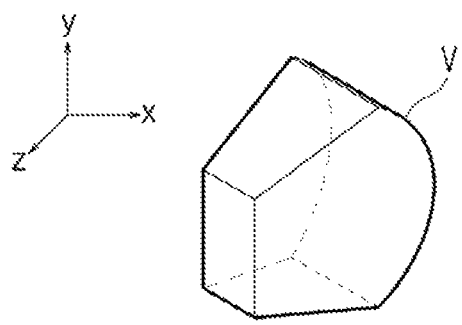
FIG. 11 is a view for describing ultrasonic volume data according to an exemplary embodiment.

FIG. 11 is a view for describing the ultrasonic volume data according to an exemplary embodiment of the present invention.

The volume data generator 70 may obtain ultrasonic volume data V indicating a three-dimensional volume, as illustrated in FIG. 11, using the two-dimensional ultrasonic image generated or compensated from the image processor 60. FIG. 11 illustrates the ultrasonic volume data V in which a plurality of fan-shaped flat surfaces are accumulated. However, the shape of the ultrasonic volume data V is not limited thereto, and may be a hexagonal shape, a cylindrical shape, a circular shape, a pyramid shape, or a cone shape.

Specifically, the volume data generator 70 may obtain the ultrasonic volume data V using various methods of properly arranging and accumulating a plurality of two-dimensional images. The volume data generator 70 may obtain a plurality of two-dimensional images using a manual scanning which traces a position and a direction of a scanning surface, a mechanical automatic scanning of the ultrasonic element 11, a transducer arranged in the two-dimensional array, or the like, and may arrange and accumulate the plurality of two-dimensional images according to the position of each image and thus may obtain the ultrasonic volume data V. The ultrasonic volume data V generated from the volume data generator 70 may be transmitted to the image processor 60 or the first storage unit 44.

The volume data generator 70 may be realized by the CPU or the GPU which may be realized by one or more semiconductor chips built in the main body 20. The volume data generator 70 may be realized by the same CPU or GPU as that of the image processor 60. According to the exemplary embodiment, the volume data generator 70 may be realized by the processor 31 of the controller 30.

Figure 12:
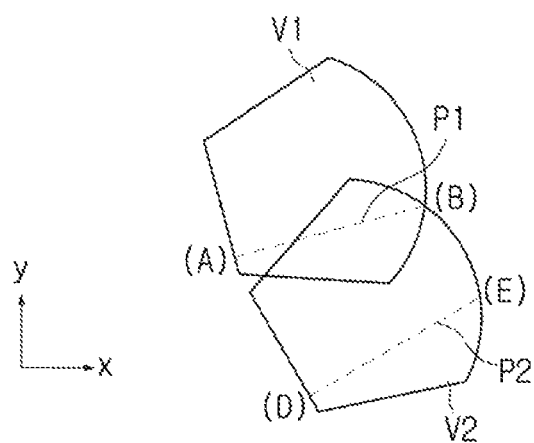
FIG. 12 is a view illustrating a plurality of pieces of ultrasonic volume data according to an exemplary embodiment.
Figure 13:
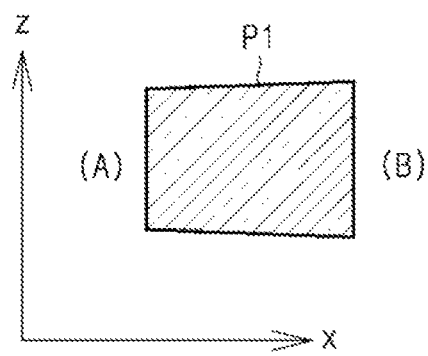
FIG. 13 is a view illustrating an ultrasonic cross-sectional image obtained from the ultrasonic volume data according to an exemplary embodiment.

FIG. 12 is a view illustrating a plurality of pieces of ultrasonic volume data according to an exemplary embodiment. FIG. 12 illustrates first ultrasonic volume data V1 and second ultrasonic volume data V2 from a z-axial direction, and illustrates the ultrasonic volume data obtained based on the ultrasonic waves which are irradiated and received at different positions and in different directions from each other. FIG. 13 is a view illustrating the ultrasonic cross-sectional image obtained from the ultrasonic volume data according to an exemplary embodiment. FIG. 13 illustrates a cross-sectional image of the first ultrasonic volume data from a y-axial direction.

When the ultrasonic volume data V generated from the volume data generator 70 is directly transmitted to the image processor 60 or transmitted to the image processor 60 through the first storage unit 44, the image processor 60 may obtain the ultrasonic cross-sectional images P1, P2, and P12 using the first ultrasonic volume data V1 obtained based on the first ultrasonic waves and the second ultrasonic volume data V2 obtained based on the second ultrasonic waves.

According to FIG. 12, the first ultrasonic volume data V1 may be obtained by the first photographing operation, and the second ultrasonic volume data V2 may be obtained by the second photographing operation. Because the first ultrasonic volume data V1 and the second ultrasonic volume data V2 have three-dimensional shapes, one or more two-dimensional cross-sectional images P1 and P2 may be obtained from the first ultrasonic volume data V1 and the second ultrasonic volume data V2. For example, as illustrated in FIG. 12, if the first ultrasonic volume data V1 is cut along a certain line, e.g., a line AB in parallel with a z-axis, a cut portion may form a section. In this case, the obtained section may be the ultrasonic cross-sectional image P1 illustrated in FIG. 13. Therefore, the ultrasonic cross-sectional image P1 may be obtained from the first ultrasonic volume data V1. In the same manner, if the second ultrasonic volume data V2 is cut along a certain line, e.g., a line DE in parallel with the z-axis, the ultrasonic cross-sectional image P2 may also be obtained from the second ultrasonic volume data V2. Hereinafter, the ultrasonic cross-sectional image obtained from the first ultrasonic volume data V1 is called a first ultrasonic cross-sectional image P1, and the ultrasonic cross-sectional image obtained from the second ultrasonic volume data V2 is called a second ultrasonic cross-sectional image P2.

Because the first ultrasonic volume data V1 and the second ultrasonic volume data V2 are photographed from the different positions and in the different directions from each other, the whole or some of both of the data may be different from each other. Therefore, even though the second ultrasonic cross-sectional image P2 is obtained along the line DE which is located at relatively the same position as that of the line AB of the first ultrasonic volume data V1, the first ultrasonic cross-sectional image P1 obtained along the line AB and the second ultrasonic cross-sectional image P2 obtained along the line DE may be different from each other. In other words, even though one of the first ultrasonic volume data V1 and the second ultrasonic volume data V2 is moved and rotated so as to coincide with each other and thus the line AB of the first ultrasonic volume data V1 and line DE of the second ultrasonic volume data V2 coincide with each other, the first ultrasonic cross-sectional image P1 and the second ultrasonic cross-sectional image P2 may be different from each other.

Figure 14:
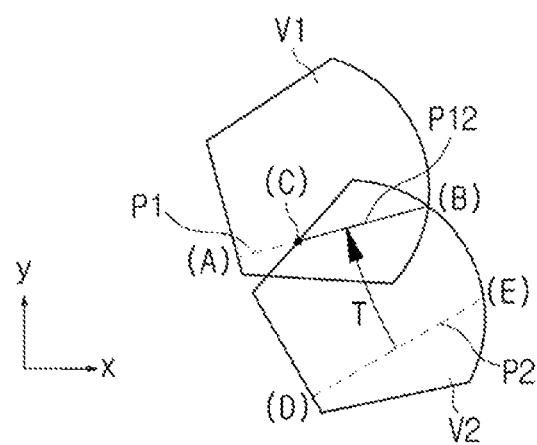
FIG. 14 is a view for describing a process of obtaining a second ultrasonic cross-sectional image coinciding with a first ultrasonic cross-sectional image obtained from the plurality of pieces of ultrasonic volume data according to an exemplary embodiment.
Figure 15:
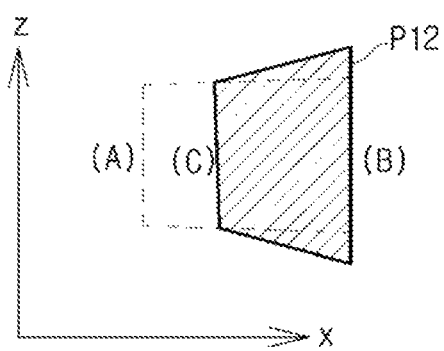
FIG. 15 is a view illustrating an example of the second ultrasonic cross-sectional image obtained by applying relationship information to second ultrasonic volume data.
Figure 16:
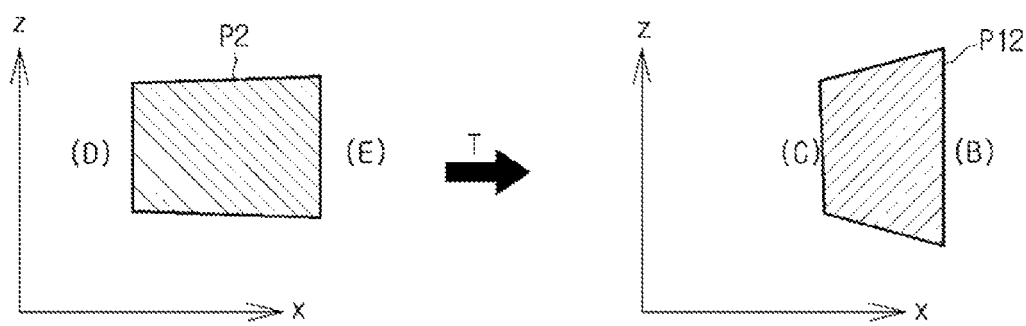
FIG. 16 is a view for describing a cross-sectional image of the second ultrasonic volume data and the second ultrasonic cross-sectional image obtained by applying the relationship information to the second ultrasonic volume data.

FIG. 14 is a view for describing a process of obtaining the second ultrasonic cross-sectional image coinciding with the first ultrasonic cross-sectional image obtained from the plurality of pieces of ultrasonic volume data according to an exemplary embodiment of the present invention. Like FIG. 12, FIG. 14 illustrates the first ultrasonic volume data V1 and the second ultrasonic volume data V2 obtained based on the ultrasonic waves, which are irradiated and received at the different positions and in the different directions, from the z-axial direction. FIG. 15 is a view illustrating an example of the second ultrasonic cross-sectional image obtained by applying the relationship information to the second ultrasonic volume data. FIG. 15 illustrates the second ultrasonic cross-sectional image obtained by applying the relationship from an axial direction. FIG. 16 is a view for describing a cross-sectional image of the second ultrasonic volume data and the second ultrasonic cross-sectional image obtained by applying the relationship information to the second ultrasonic volume data. FIG. 16 illustrates the second ultrasonic cross-sectional image and the second ultrasonic cross-sectional image obtained by applying the relationship information, from the axial direction.

The relationship information obtained from the relationship information computation part 33 may include a conversion T by which the one cross section P1 of the first ultrasonic volume data V1 by the first ultrasonic waves u1 coincides with the one cross section P2 of the second ultrasonic volume data V2 by the second ultrasonic waves u2. The conversion T may be computed by the above-mentioned Equation 1. In other words, the conversion T may be obtained according to the relationship between the first position and direction of the ultrasonic probe receiving the first ultrasonic waves and the second position and direction of the ultrasonic probe receiving the second ultrasonic waves. As illustrated in FIG. 12, when the first position and the first direction of the first ultrasonic waves u1 are different from the second position and the second direction of the second ultrasonic waves u2, the conversion T may be obtained using all of the first position, the first direction, the second position, and the second direction. In this case, the conversion may be expressed mathematically in the form of a 6×6 matrix, but is not limited thereto.

As illustrated in FIG. 14, the conversion T may move a position of the line DE for obtaining the second ultrasonic cross-sectional image P2 to the same position as or a similar position to that of the line AB for obtaining the first ultrasonic cross-sectional image P1. In other words, the line DE for obtaining the second ultrasonic cross-sectional image P2 may be converted into a line BC. As illustrated in FIG. 15, the second ultrasonic cross-sectional image P12 may be obtained along the ling BC from the second ultrasonic volume data V2. In other words, as illustrated in FIG. 16, the second ultrasonic cross-sectional image P2 may be changed into another second ultrasonic cross-sectional image P12 by the conversion T. Because the second ultrasonic cross-sectional image P12 is the same as the first ultrasonic cross-sectional image P1 or shares an adjacent surface with the first ultrasonic cross-sectional image P1, the whole or a part of the second ultrasonic cross-sectional image P12 may be the same as or similar to the whole or a part of the first ultrasonic cross-sectional image P1. Therefore, because the user may obtain the second ultrasonic cross-sectional image P2 at the second ultrasonic photographing operation, which is the same as or similar to the first ultrasonic cross-sectional image P1 obtained at the first ultrasonic photographing operation, it is possible to easily compare the same or similar portions. Therefore, when the user such as a doctor performs the first ultrasonic photographing operation before a procedure and then performs the second ultrasonic photographing operation after the procedure, it is possible to compare the same or similar portions with each other, and thus to easily determine a result of the procedure.

The applying of the relationship information to the second ultrasonic volume data V2 and the obtaining of the second ultrasonic cross-sectional image P12 may be performed by the image processor 60.

According to the exemplary embodiment, the second ultrasonic cross-sectional image P12 obtained by the conversion may be transmitted to and then stored in the first storage unit 44, or may be transmitted to the displaying part 24 of the output part 21 and then displayed to the user. The second ultrasonic cross-sectional image P12 obtained by the conversion may be transmitted to the displaying part 24 of the output part 21 in order to be displayed to the user, after being transmitted to and then stored in the first storage unit 44.

The first storage unit 44 may temporarily or non-temporarily store the ultrasonic image and the cross-sectional image P12 generated from the image processor 60 or the ultrasonic volume data V generated from the volume data generator 70. The ultrasonic image or the like stored in the first storage unit 44 may be displayed on the displaying part 24 or may be transmitted to other storage units (not shown) according to the user's instruction input through the input part 25 or the previously defined set. If necessary, the ultrasonic image or the like stored in the first storage unit 44 may be transmitted to the workstation (not shown) connected to the ultrasonic imaging apparatus 1. Further, the ultrasonic image or the like stored in the first storage unit 44 may be transmitted to an external server or the like through a wired or wireless network. The server may transmit the received ultrasonic image or the like to a separate terminal such as a desktop computer, a smartphone, a cellular phone, a tablet computer, a notebook computer, and a personal digital assistance (PDA) through the wired or wireless network.

The input part 25 may output an electrical signal according to the user's operation. The output electrical signal may be transmitted to the controller 30. The controller 30 may generate a control signal corresponding to the received electrical signal, and then may transmit the generated control signal to each component of the ultrasonic imaging apparatus 1. Therefore, the ultrasonic imaging apparatus 1 may receive various commands related to the controlling of the ultrasonic imaging apparatus 1 from the user. For example, the input part 25 may include at least one of a physical button, a keyboard, a mouse, a track ball, a touchscreen, a touchpad, a paddle, various levers, a handle, and a stick-type operating device. Also, the input part 25 may include various other input means.

The detector 26 may detect the position and/or direction of the ultrasonic probe 10. The detector 26 may detect the position and/or direction of the ultrasonic probe 10 through various methods.

According to an exemplary embodiment, the detector 26 may include an electromagnetic forming unit (26a of FIG. 6) and the electromagnetic sensor (not shown). The electromagnetic forming unit 26a may form an electromagnetic field at a desired area in which the ultrasonic probe 10 is located. The electromagnetic sensor may detect the electromagnetic field and thus may trace the position and/or direction of the ultrasonic probe 10. For example, the electromagnetic sensor may output a signal of a relative position of the ultrasonic probe 10 and/or a signal indicating a vector value of the direction of the ultrasonic probe 10 according to a detecting result of the electromagnetic field, and thus may detect the position and/or the direction of the ultrasonic probe 10. The electromagnetic sensor may be installed at the ultrasonic probe 10.

According to an exemplary embodiment, the detector 26 may include an optical sensor. The optical sensor may photograph a predetermined area in which the ultrasonic probe 10 is located, and thus may detect the position and/or the direction of the ultrasonic probe 10 from the photographed image. Also, the optical sensor may photograph a light emitting object such as a light emitting diode or a marker, which is installed at the ultrasonic probe 10, and thus may detect the position and/or the direction of the ultrasonic probe 10. The optical sensor may be realized using a visible light sensor or an infrared sensor.

According to an exemplary embodiment, the detector 26 may include a motion sensor. The motion sensor may include an acceleration sensor. The motion sensor may be installed at the ultrasonic probe 10. The motion sensor may detect the movement of the ultrasonic probe 10, may output a signal corresponding to the detected movement, and thus may detect the position and/or the direction of the ultrasonic probe 10.

According to an exemplary embodiment, the detector 26 may include a first communication module, and the first communication module may perform communication with a second communication module installed at the ultrasonic probe 10. The first communication module may measure a distance of the ultrasonic probe 10 using an intensity of a signal or the like, while performing the communication with the second communication module. A plurality of first communication modules may be provided, and each of the plurality of first communication modules may obtain the distance with the ultrasonic probe 10. When the distance between the ultrasonic probe 10 and each of the plurality of first communication modules is obtained, a processor provided in the detector 26 or the controller 30 provided at the main body 20 may synthesize the obtained distances and thus may recognize the position of the ultrasonic probe 10.

The output part 21 may include at least one of the sound output part 22 which outputs a sound, a lighting part 23 which emits predetermined light, and the displaying part 24 which displays a predetermined image.

The sound output part 22 such as a speaker may convert the electrical signal into a sound signal including an audio signal, and then may output the sound such as a voice to the user. The sound output part 22 may inform the user of information of a state of the ultrasonic imaging apparatus 1 or a relevant warning message thereof using various sounds such as a beep sound, and thus may allow the user to easily operate or use the ultrasonic imaging apparatus 1.

The lighting part 23 may output light having a predetermined color according to applied power. The lighting part 23 may turn on and off the light having the predetermined color according to a predetermined pattern, and may also change the color of the light. The output color of the light may be changed according to a predetermined pattern. The lighting part 23 may output the light according to the predetermined pattern to transmit the information of the state of the ultrasonic imaging apparatus 1 or the relevant warning message thereof to the user, and thus may allow the user to easily operate or use the ultrasonic imaging apparatus 1. The lighting part 23 may be realized using the light emitting diode.

The displaying part 24 may display the ultrasonic image, the cross-sectional image p12, or the ultrasonic volume data V to the user. The displaying part 24 may be realized using a plasma display panel (PDP), a light emitting diode panel, an organic light emitting diode (OLED) panel, a liquid crystal display (LCD), or the like. In addition, the displaying part 24 may be realized using various means which can display an image. Further, the displaying part 24 may use a three-dimensional display unit which displays a three-dimensional image. According to the exemplary embodiment, the displaying part 24 may include a touchscreen unit. When the displaying part 24 includes the touchscreen unit, the displaying part 24 may also perform a function of the input part 25. Here, the touchscreen unit may be realized using a resistive touchscreen panel or a capacitive touchscreen panel. Further, the touchscreen unit may be realized using a touchscreen panel using ultrasonic waves or infrared rays.

Figure 17:
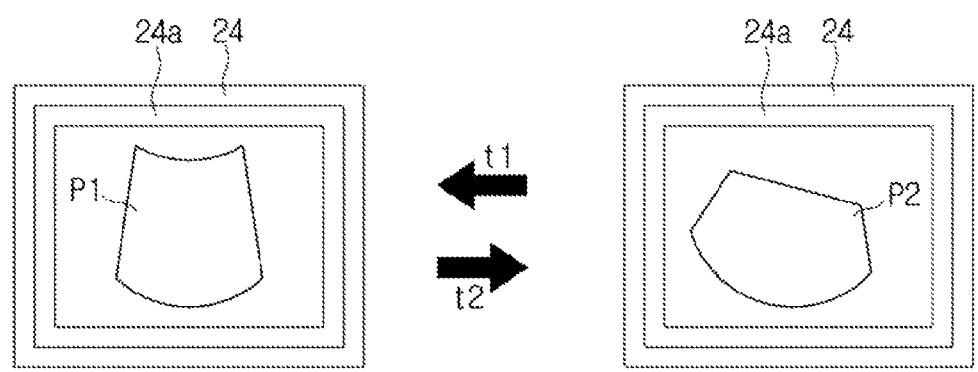
FIGS. 17 to 19 are views illustrating a display screen according to an exemplary embodiment.
Figure 18:
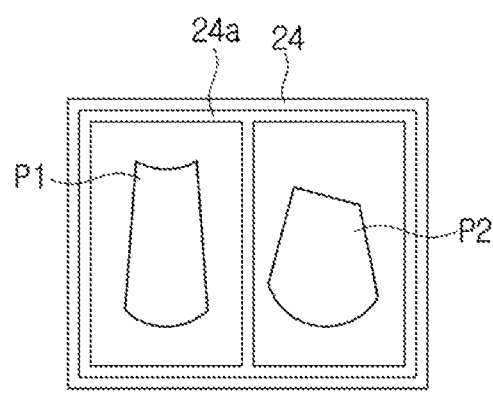
Figure 19:
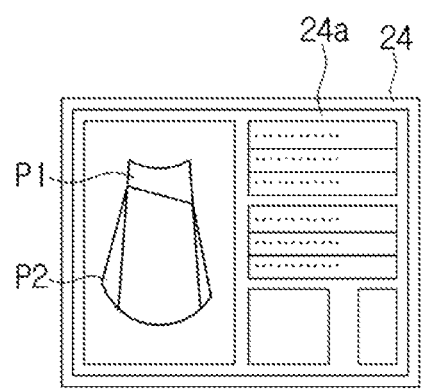

FIGS. 17 to 19 are views illustrating a display screen displayed on the displaying part according to an exemplary embodiment of the present invention.

As illustrated in FIGS. 17 to 19, the displaying part 24 may include a display screen 24a which displays an image using the PDP, the light emitting diode panel, the OLED panel, the LCD, or the like. Various images may be displayed on the display screen 24a. For example, at least one of the first ultrasonic image, the second ultrasonic image, the first ultrasonic cross-sectional image P1, the second ultrasonic cross-sectional image P2, the first ultrasonic volume data V1, and the second ultrasonic volume data V2 may be displayed thereon.

Referring to FIG. 17, the displaying part 24 may display, in turn, the first ultrasonic cross-sectional image P1 and the second ultrasonic cross-sectional image P2 obtained using the conversion T on the display screen 24a. When the two images P1 and P2 are displayed, the displaying part 24 may alternately display the two images P1 and P2. In other words, the displaying part 24 may display the first ultrasonic cross-sectional image P1 and then may display the second ultrasonic cross-sectional image P2 after a predetermined period of time t1 or when the user operates the input part 25. As described above, after the second ultrasonic cross-sectional image P2 is displayed, the displaying part 24 may display again the first ultrasonic cross-sectional image P1 after a predetermined period of time t2 or when the user operates the input part 25. According to the exemplary embodiment, the first ultrasonic cross-sectional image P1 may be displayed first, and then the second ultrasonic cross-sectional image P2 may be displayed later. On the contrary, the second ultrasonic cross-sectional image P2 may be displayed first, and then the first ultrasonic cross-sectional image P1 may be displayed later. When the displaying part 24 displays a plurality of, e.g., three or more images, the three or more images may be displayed in turn according to a predetermined order.

Referring to FIG. 18, the displaying part 24 may display the first ultrasonic cross-sectional image P1 and the second ultrasonic cross-sectional image P2 obtained using the conversion T in parallel on the display screen 24a. In this case, for example, the displaying part 24 may display one P1 of the images on a left side, and may display the other P2 on a right side. However, positions at which the images P1 and P2 are displayed on the display screen 24a may be arbitrarily determined by the system designer. The positions at which each of the images P1 and P2 is displayed on the display screen 24a may be changed according to a predetermined set or the user's operation.

As illustrated in FIG. 19, the displaying part 24 may display an overlapped image obtained by overlapping the first ultrasonic cross-sectional image P1 with the second ultrasonic cross-sectional image P2 obtained using the conversion T. In this case, the overlapped image may be generated from the image processor 60.

Figure 20:
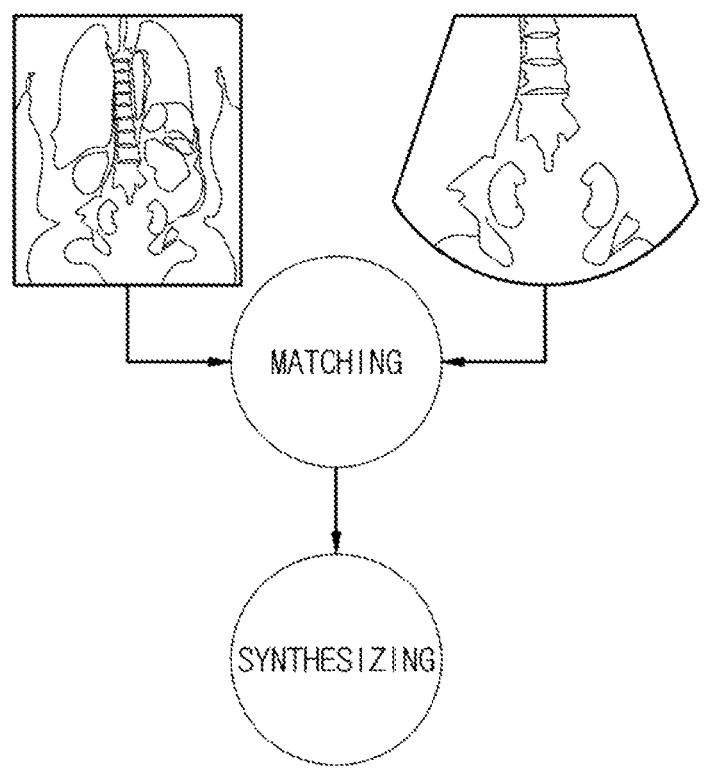
FIG. 20 is a view for describing an image matching according to an exemplary embodiment.

FIG. 20 is a view for describing an image matching.

The displaying part 24 may display an image synthesized using a matching. Referring to FIG. 20, the synthesized image may be obtained by matching and synthesizing the plurality of images 99 and P2 along points corresponding to each other. For example, the synthesized image may be obtained by matching the plurality of images using feature points in the images and then synthesizing the plurality of matched images. Here, the synthesized image may be an image obtained by matching and synthesizing the second ultrasonic cross-sectional image P2 and the image 99 obtained by other imaging apparatus such as a magnetic resonance imaging (MRI) apparatus, a radiation imaging apparatus, and a computed tomography (CT) apparatus.

Hereinafter, an exemplary embodiment of the ultrasonic imaging apparatus will be described with reference to FIGS. 21 and 22.

Figure 21:
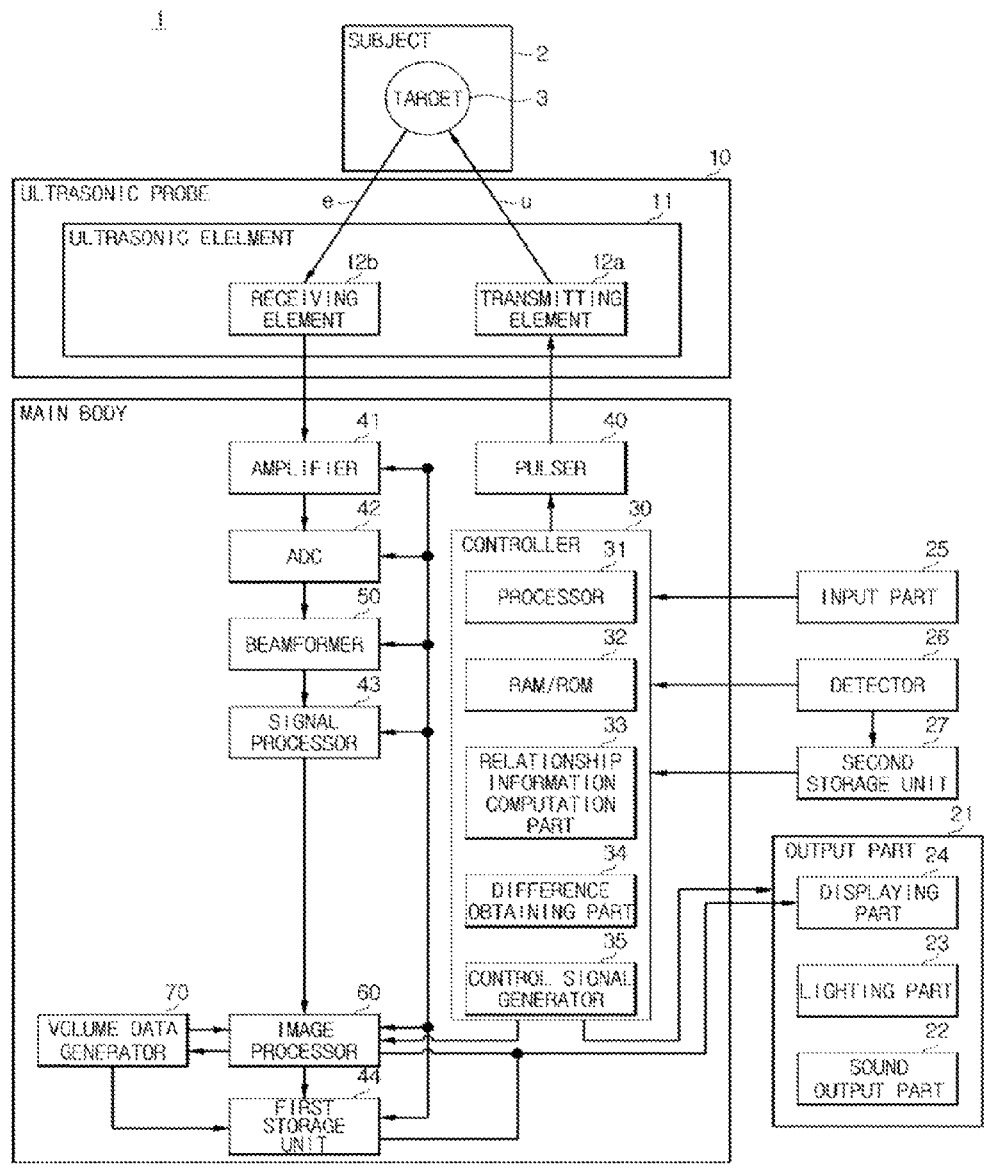
FIG. 21 is a block diagram of an ultrasonic imaging apparatus according to an exemplary embodiment.

FIG. 21 is a block diagram of an ultrasonic imaging apparatus according to an exemplary embodiment of the present invention.

Referring to FIG. 21 an ultrasonic imaging apparatus 4 according to an exemplary embodiment includes an ultrasonic probe 10 which receives ultrasonic waves irradiated from a target 3 in a subject 2, a main body 20 which generates an ultrasonic image using a signal output from the ultrasonic probe 10 or controls the ultrasonic probe 10 or various components according to a user's instruction, and a detector 26 which detects a position of the ultrasonic probe 10.

Because the subject 2, the target 3, and the ultrasonic probe 10 may be the same as those described in FIGS. 1 to 9, the description thereof will be omitted. Of course, according to the exemplary embodiment, the subject 2, the target 3, and the ultrasonic probe 10 of the ultrasonic imaging apparatus 4 according to an exemplary embodiment may be different from those of the ultrasonic imaging apparatus 1 according to an exemplary embodiment within a range which would be considered by a person skilled in the art.

The main body 20 may include a controller 30, a pulser 40, an amplifier 41, an analog-to-digital converter 42, a beamformer 50, a signal processor 43, a first storage unit 44, an image processor 60, and a volume data generator 70. If necessary, some of them may be omitted. Also, some of them may be provided at the ultrasonic probe 10, or may be provided at a separate workstation (not shown).

The controller 30 of the main body 20 may include a processor 31, a RAM or ROM 32, a relationship information computation part 33, a difference obtaining part 34, and a control signal generator 35. Because the processor 31, the RAM or ROM 32, and the relationship information computation part 33 may be the same as those described with reference to FIG. 2, the detailed description thereof will be omitted. Of course, according to the exemplary embodiment, the processor 31, the RAM or ROM 32, and the relationship information computation part 33 may be different within a range which would be considered by a person skilled in the art.

The difference obtaining part 34 may obtain a difference between a position and/or direction of an ultrasonic probe 101 at a first photographing operation and a position and/or direction of an ultrasonic probe 102 at a second photographing operation based on data of at least one of a position and a direction of the ultrasonic probe 10 transmitted to the detector 26 or a storage part 27. The difference obtaining part 34 may obtain an error between a first position and a second position and/or an error between a first direction and a second direction, and thus may obtain the difference. In this case, for example, the difference obtaining part 34 may perform a calculation in which each value of the first position and direction of ultrasonic probe 101 receiving first ultrasonic waves is deducted by each value of the second position and direction of the ultrasonic probe 102 receiving second ultrasonic waves, and thus may obtain the error between the first position and the second position and/or the error between the first direction and the second direction. The difference obtained from the difference obtaining part 34 may be transmitted to the control signal generator 35.

The control signal generator 35 may compare the received error with a reference value, may generate a control signal corresponding to a comparing result, and may transmit the generated control signal to an output part 21 or the ultrasonic probe 10.

Specifically, the control signal generator 35 may compare the difference between the position and/or direction of the ultrasonic probe 101 at the first photographing operation and the position and/or direction of the ultrasonic probe 102 at the second photographing operation with an error range which is the reference value determined by the system designer or the user. When the difference is within the error range, the control signal generator 35 may not generate any control signal. When the difference between the position and/or direction of the ultrasonic probe 101 at the first photographing operation and the position and/or direction of the ultrasonic probe 102 at the second photographing operation exceeds the error range, the control signal generator 35 may generate a control signal and then may transmit the generated control signal to the output part 21 or the ultrasonic probe 10.

Here, the error range may be determined to a proper value. For example, when the error range is too narrow, because the user should operate precisely the ultrasonic probe 10, it may be inconvenient for the user to use the ultrasonic probe 10. Also, when the error range is too wide, a difference between a first ultrasonic cross-sectional image P1 and a second ultrasonic cross-sectional image P2 may be excessively increased. Therefore, the error range may be set appropriately and variously according to characteristics and kinds of the ultrasonic imaging apparatus 4, a shape of the ultrasonic probe 10, precision of the ultrasonic image to be obtained, kinds of the subject 2 or the target 3, or the like. The error range may be changed through an operation of an input part 25 by the user.

The output part 21 may be operated to output a signal which induces a change in at least one of the position and the direction of the ultrasonic probe 102 at the second photographing operation according to the control signal transmitted from the control signal generator 35. For example, a sound output part 22 may output a beep sound according to the control signal transmitted to the output part 21, and a lighting part 23 may output light having a predetermined color according to a predetermined pattern, and a displaying part 24 may display a warning message related to the difference, or the like. A loudness level and a length of the beep sound or the color or pattern of the light output from the lighting part 23 may be different according to a degree in which the difference exceeds the error range. In addition, the sound output part 22, the lighting part 23, or the displaying part 24 may be operated according to various methods, which would be considered by a person skilled in the art, so as to inform the user of the difference between the position and/or direction of the ultrasonic probe 101 at the first photographing operation and the position and/or direction of the ultrasonic probe 102 at the second photographing operation.

Hereinafter, an example of a display screen 24a which is output by the displaying part 24 when the difference occurs will be described. FIG. 22 is a view illustrating the displaying part which displays an ultrasonic probe movement guide according to an exemplary embodiment of the present invention.

Figure 22:
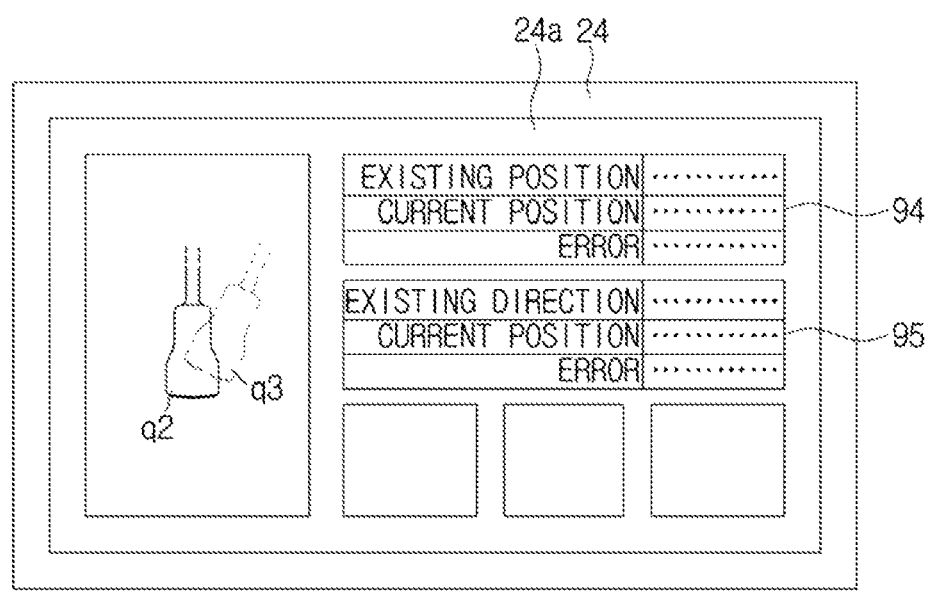
FIG. 22 is a view illustrating a displaying part which displays an ultrasonic probe movement guide.

Referring to FIG. 22, the display screen 24a of the displaying part 24 may include at least one of a symbol displaying image 96 which displays the difference through a predetermined symbol, and numerical value displaying images 94 and 95 which display the difference numerically.

The symbol displaying image 96 may include a symbol 92 which indicates the position of the ultrasonic probe 101 at the first photographing operation, and a symbol 93 which indicates the position of the ultrasonic probe 102 at a current photographing operation, i.e., the second photographing operation. Here, the symbols 92 and 93 may be expressed by various shapes, such as an arrow shape and a triangular shape, which express the position and the direction together. The symbols 92 and 93 may include letters.

The numerical value displaying images 94 and 95 may include a position indicating image 94 and a direction indicating image 95. The position indicating image 94 may display a numerical value indicating the first position at the first photographing operation and a numerical value indicating the second position at the second photographing operation of the ultrasonic probes 101 and 102. The direction indicating image 95 may display a numerical value indicating the first direction at the first photographing operation and a numerical value indicating the second direction at the second photographing operation of the ultrasonic probes 101 and 102. Further, the position indicating image 94 and the direction indicating image 95 may further display a numerical value indicating a position difference and a direction difference.

The user may visually check the difference between the second position and/or the second direction of the ultrasonic probe 102 at the current photographing operation and the first position and/or the first direction of the ultrasonic probe 101 at the first photographing operation using at least one of the symbol displaying image 96 and the numerical value displaying images 94 and 95.

Until now, an example of the display screen 24*a* has been described. However, the displaying part 24 may display the position and/or the direction of the ultrasonic probe 101 at the first photographing operation, the position and/or the direction of the ultrasonic probe 102 at the second photographing operation, and the difference therebetween.

The ultrasonic probe 10 may also be operated according to the control signal transmitted from the control signal generator 35. For example, when the difference exceeds the error range, the ultrasonic probe 10 may be vibrated according to the control signal transmitted from the control signal generator 35, and then may inform the user of the difference between the position and/or direction of the ultrasonic probe 101 at the first photographing operation and the position and/or direction of the ultrasonic probe 102 at the second photographing operation. In this case, the vibration of the ultrasonic probe 10 may be performed by a vibrator installed at the ultrasonic probe 10. The ultrasonic probe 10 may be vibrated differently according to a degree in which the difference exceeds the error range.

Because the pulser 40, the amplifier 41, the analog-to-digital converter 42, the beamformer 50, the signal processor 43, the first storage unit 44, the image processor 60, and the volume data generator 70 of the main body 20 may be the same as those described through FIGS. 1 to 20, the detailed description thereof will be omitted. Of course, according to the exemplary embodiment, the pulser 40, the amplifier 41, the analog-to-digital converter 42, the beamformer 50, the signal processor 43, the first storage unit 44, the image processor 60, and the volume data generator 70 of the main body 20 may be partly different within a range which would be considered by a person skilled in the art.

Hereinafter, a method of controlling an ultrasonic imaging apparatus will be described with reference to FIGS. 23A to 24. The method will be described based on a method of controlling the ultrasonic imaging apparatus which irradiates the ultrasonic waves to the inner side of the subject, receives the ultrasonic waves reflected from the target in the subject, and then generates the ultrasonic image based on the received ultrasonic waves. However, the method of controlling the ultrasonic imaging apparatus is not limited to the above-mentioned ultrasonic imaging apparatus, and may be equally or modifiedly applied to the photoacoustic ultrasonic apparatus using the photoacoustic spectroscopy and the Doppler sonography apparatus using the Doppler effect. Also, the method may be equally or modifiedly applied to other various apparatuses which generate an image using the ultrasonic waves.

Figure 23A:
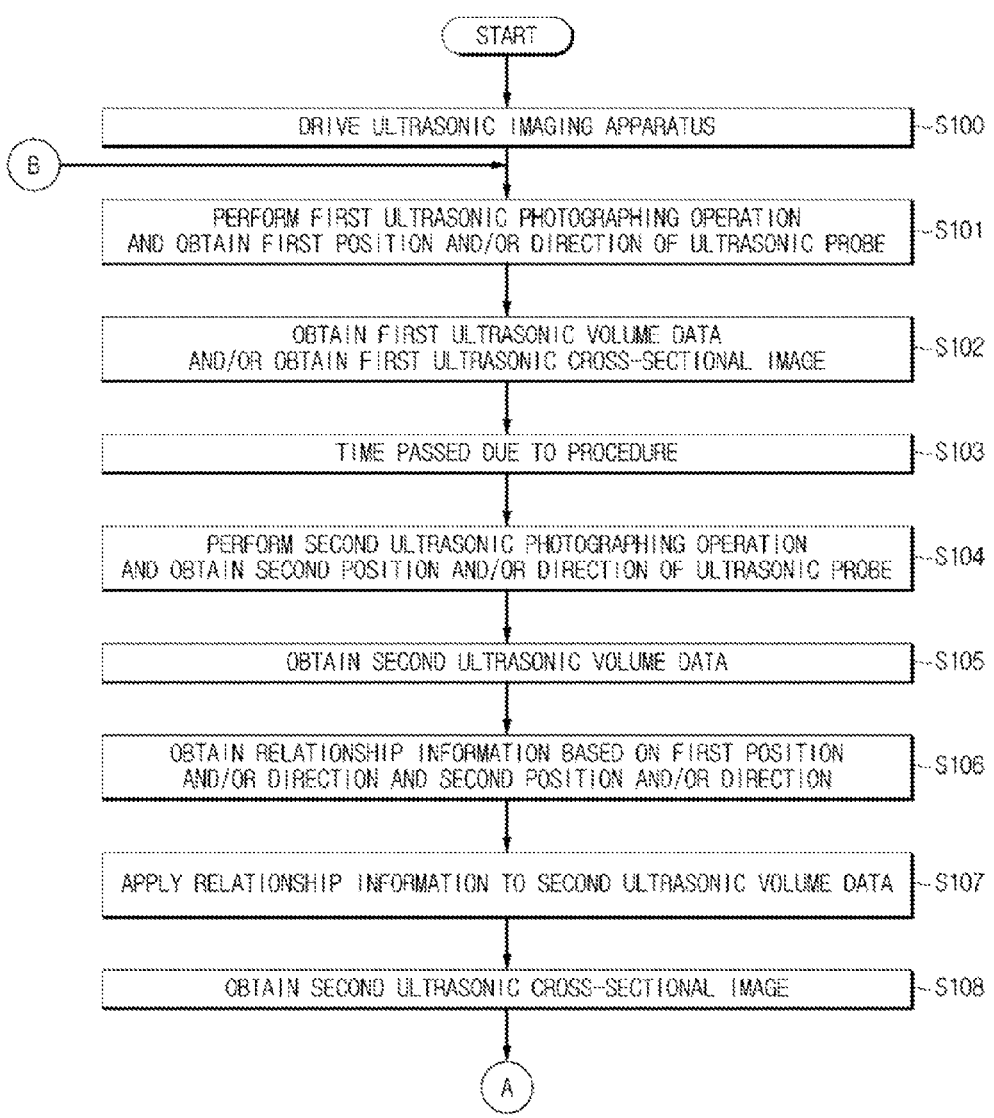
FIGS. 23A and 23B are flowcharts illustrating a method of controlling the ultrasonic imaging apparatus according to an exemplary embodiment.
Figure 23B:
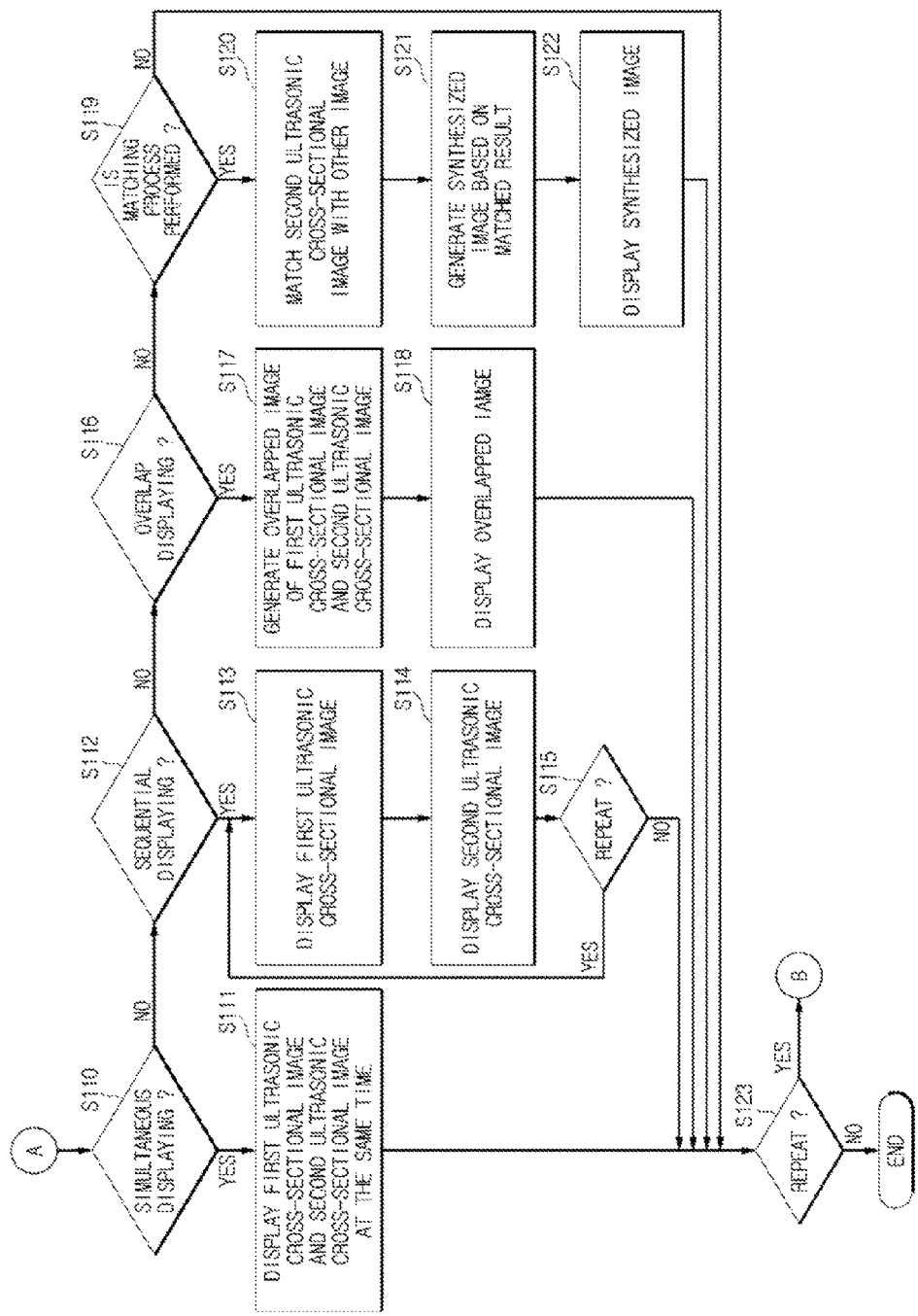

FIGS. 23A and 23B are flowcharts illustrating the method of controlling the ultrasonic imaging apparatus according to an exemplary embodiment of the present invention.

According to FIG. 23A, first, the ultrasonic imaging apparatus may be started to be driven according to a user' operation (s100). In this case, the subject may be located at a position in which an image of the target therein is obtained by the ultrasonic probe 10.

The ultrasonic waves are irradiated on the target in the subject according to the user's operation, and the ultrasonic probe receives the ultrasonic waves reflected from the target in the subject, and thus the ultrasonic photographing operation is primarily performed. Meanwhile, the ultrasonic waves may be irradiated, and at least one of the first position and the first direction of the ultrasonic probe receiving the reflected ultrasonic waves may be measured (s101). The at least one of the first position and the first direction of the ultrasonic probe may be detected by the above-mentioned detector. The detector may include at least one of an electromagnetic sensor, an optical sensor, a motion sensor, and a first communication module communicating with a second communication module installed at the ultrasonic probe.

When the first ultrasonic photographing operation is performed, at least one of the first ultrasonic volume data and the first ultrasonic cross-sectional image may be obtained (s102). The first ultrasonic cross-sectional image may include one or two or more cross sections of the first ultrasonic volume data.

The first ultrasonic photographing operation is completed, and time may pass due to a procedure or the like (s103).

After time passed and the procedure is completed, the second ultrasonic photographing operation may be performed. In this case, the ultrasonic waves are also irradiated on the target in the subject according to the user's operation in the same manner as in the first photographing operation, and the ultrasonic probe receives the ultrasonic waves reflected from the target in the subject, and thus the ultrasonic photographing operation may be formed. At the same time, at least one of the second position and the second direction of the ultrasonic probe may be obtained (s104). Here, the first and second positions or the first and second directions may be different from each other. Of course, both of the first and second positions and the first and second directions may be different from each other.

At least one of the second position and the second direction of the ultrasonic probe may be detected by the detector. The detector may include at least one of the electromagnetic sensor, the optical sensor, the motion sensor, and the first communication module communicating with the second communication module installed at the ultrasonic probe. The detector which detects the at least one of the second position and the second direction may be the same as or different from that which detects the at least one of the first position and the first direction. Also, the detector which detects the at least one of the second position and the second direction may be the same kind as or a different kind from that which detects the at least one of the first position and the first direction.

When the second ultrasonic photographing operation is performed, the second ultrasonic volume data may be obtained using the obtained ultrasonic waves (s105).

Meanwhile, the relationship information may be obtained using at least one of the first position and the first direction and at least one of the second position and the second direction (s106). The relationship information may include a conversion by which one cross section of the first ultrasonic volume data by the first ultrasonic waves coincides with one cross section of the second ultrasonic volume data by the second ultrasonic waves.

The operation s106 may be performed before or after the operation s105. Further, the operations s105 and s106 may be performed at the same time.

When the relationship information is obtained, the relationship information is applied to the second ultrasonic volume data (s107), and thus the second ultrasonic cross-sectional image may be obtained as illustrated in FIG. 15 (s108).

As described above, after the second ultrasonic cross-sectional image is obtained, the first and second ultrasonic cross-sectional images may be variously displayed according to a preset method.

Hereinafter, the various methods of displaying the first and second ultrasonic cross-sectional images will be described with reference to FIG. 23B. FIG. 23B illustrates that whether to be displayed at the same time (s110), whether to be displayed sequentially (s112), whether to be displayed overlappingly (s116), and whether to display a synthetic image (s119) are determined in turn. However, such a determination order may be determined arbitrarily according to an algorithm designed by the system designer. Also, some of them may be omitted by selection of the user, or a new displaying method may be added. Each of a simultaneous displaying (hereinafter s110), a sequential displaying (hereinafter s112), an overlap displaying (hereinafter s116), and a synthesized image displaying (hereinafter s119) may be realized in a predetermined mode. The user may select one of a plurality of modes and thus may select the method of displaying the first and second ultrasonic cross-sectional images through the ultrasonic imaging apparatus.

According to FIG. 23B, when the first and second ultrasonic cross-sectional images are displayed at the same time (s110), the first and second ultrasonic cross-sectional images may be displayed on one display screen (s111), as illustrated in FIG. 18. In this case, the first and second ultrasonic cross-sectional images may be displayed in parallel.

When the first and second ultrasonic cross-sectional images are sequentially displayed (s112), the first ultrasonic cross-sectional image may be first displayed on the display screen (s113), the displaying of the first ultrasonic cross-sectional image may be stopped, and then the second ultrasonic cross-sectional image may be displayed (s114), as illustrated in FIG. 17. In this case, the second ultrasonic cross-sectional image may be first displayed, and then the first ultrasonic cross-sectional image may be displayed later. This process may be repeated according to a previously defined set or the user's selection (s115).

When the first and second ultrasonic cross-sectional images are displayed to be overlapped with each other (s116), first, an overlapped image in which the first and second ultrasonic cross-sectional images are overlapped with each other may be generated (s117). In this case, the overlapped image may be generated by applying the same transparency to both of the first ultrasonic cross-sectional image and the second ultrasonic cross-sectional image, or may be generated by applying different transparency to both of them (s118).

When a matching process is performed and thus the synthesized image is generated (s119), first, the second ultrasonic cross-sectional image may be matched with other image (s120), and then the synthesized image may be generated based on the matching result (s121). Here, the other image may include a magnetic resonance image obtained by the magnetic resonance imaging (MRI) apparatus, and a radiographic image obtained by the computed tomography (CT) apparatus or the radiation imaging apparatus, or the first ultrasonic cross-sectional image. When the synthesized image is obtained, the obtained synthesized image may be displayed on the display screen (s122).

The above-mentioned operations s101 to s122 may be repeated according to a previously defined set or the user's selection (s123).

Figure 24:
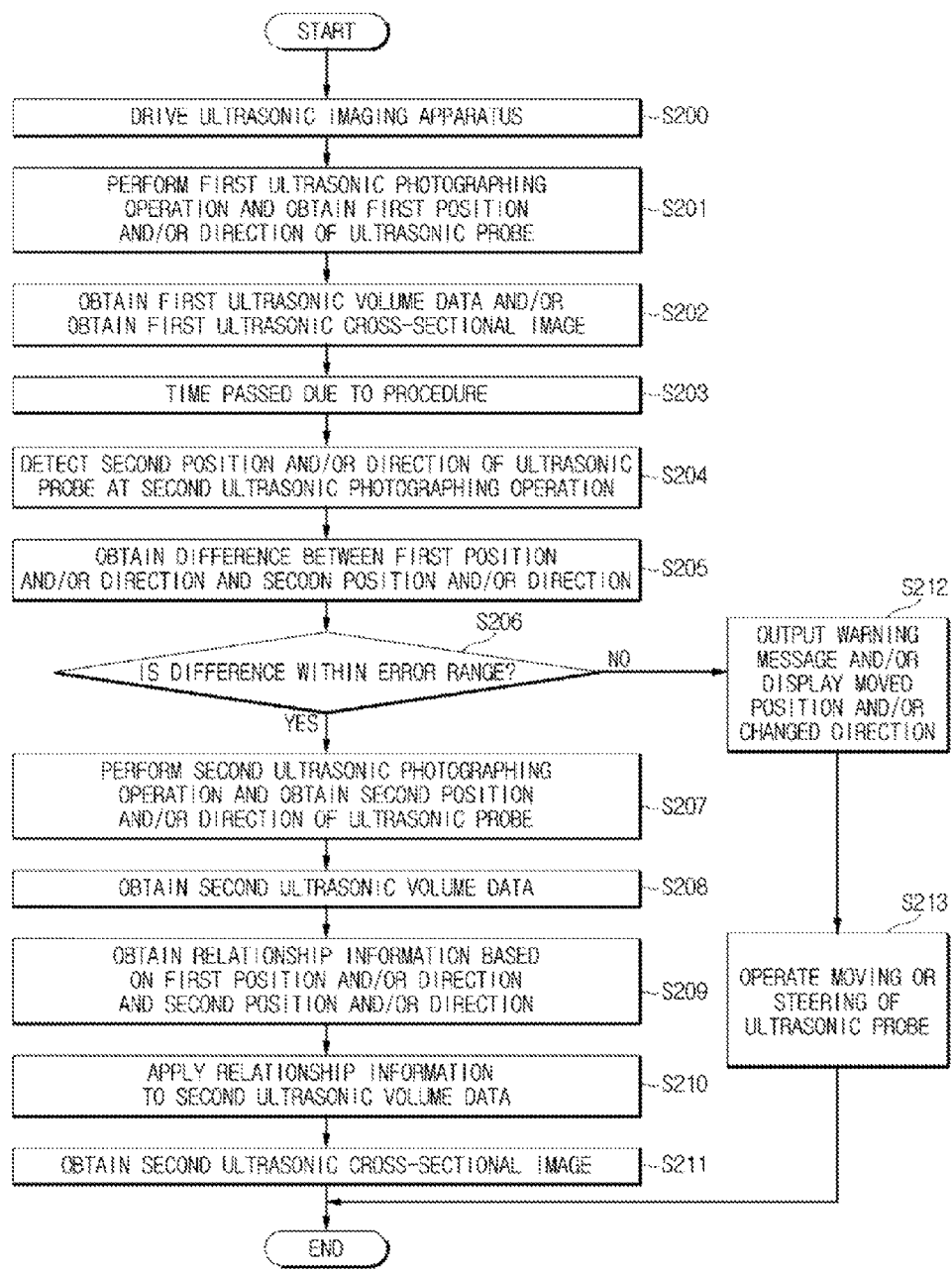
FIG. 24 is a flowchart illustrating a method of controlling the ultrasonic imaging apparatus according to an exemplary embodiment.

FIG. 24 is a flowchart illustrating a method of controlling the ultrasonic imaging apparatus according to an exemplary embodiment of the present invention.

According to FIG. 24, first, the ultrasonic imaging apparatus may be started to be driven according to a user' operation (s200).

The ultrasonic probe may irradiate the ultrasonic waves on the target in the subject according to the user's operation, may receive the ultrasonic waves reflected from the target in the subject, and thus may perform the first ultrasonic photographing operation. Further, at least one of the first position and the first direction of the ultrasonic probe receiving the reflected ultrasonic waves may be measured (s201). The at least one of the first position and the first direction of the ultrasonic probe may be detected by the above-mentioned detector. The detector may include at least one of an electromagnetic sensor, an optical sensor, a motion sensor, and a first communication module communicating with a second communication module installed at the ultrasonic probe.

When the first ultrasonic photographing operation is performed, at least one of the first ultrasonic volume data and the first ultrasonic cross-sectional image may be obtained (s202). The first ultrasonic cross-sectional image may include one or two or more cross sections of the first ultrasonic volume data.

After the first ultrasonic photographing operation is completed and time may pass due to a procedure or the like (s203), the user may perform the second ultrasonic photographing operation to obtain an ultrasonic image of the inner side of the subject.

When the second ultrasonic photographing operation is performed, the user may move the ultrasonic probe to a position in which the ultrasonic waves are irradiated on the target to be photographed. For example, the user may allow the ultrasonic probe to be in contact with an outer surface of the subject. As described above, when the position of the ultrasonic probe is moved, the detector may detect at least one of the second position and the second direction of the ultrasonic probe (s204).

The at least one of the second position and the second direction of the ultrasonic probe may be detected by the detector. The detector may include at least one of the electromagnetic sensor, the optical sensor, the motion sensor, and the first communication module communicating with the second communication module installed at the ultrasonic probe. The detector which detects the at least one of the second position and the second direction may be the same as or different from that which detects the at least one of the first position and the first direction. Also, the detector which detects the at least one of the second position and the second direction may be the same kind as or a different kind from that which detects the at least one of the first position and the first direction.

When the detector detects at least one of the second position and the direction, the ultrasonic imaging apparatus may compare the first position with the second position or the first direction with the second direction, or may compare both of them so as to obtain a difference in at least one of the position and the direction.

When the difference is obtained, the ultrasonic imaging apparatus may determine whether the difference is within the error range (s206).

When the difference is within the error range, the ultrasonic probe at the second photographing operation is disposed at the same position as or a position adjacent to the ultrasonic probe at the first photographing operation, and it is also determined that the ultrasonic probe at the second photographing operation is disposed in the same direction as or a direction adjacent to the ultrasonic probe at the first photographing operation, and the photographing operation may be performed according to the user's operation or a previously defined set (s207). As a result, the second ultrasonic volume data may be obtained (s208).

In this case, if necessary, at least one of the second position and the second direction at the second photographing operation may be obtained again. Of course, when at least one of the second position and the second direction is obtained in the operation s204, the at least one of the second position and the second direction at the second photographing operation may not be obtained again.

Meanwhile, the relationship information may be computed at the same time with the second ultrasonic photographing operation or sequentially using the at least one of the first position and the first direction and the at least one of the second position and the second direction (s209). The relationship information may include a conversion by which one cross section of the first ultrasonic volume data by the first ultrasonic waves coincides with one cross section of the second ultrasonic volume data by the second ultrasonic waves.

The operation s209 may be performed before or after the operation s208. Further, the operations s209 and s208 may be performed at the same time.

When the relationship information is obtained as described above, the obtained relationship information may be applied to the second ultrasonic volume data (s210), and thus the second ultrasonic cross-sectional image may be obtained, as illustrated in FIG. 15 (s211). The obtained second ultrasonic cross-sectional image may be displayed to the user in various methods as illustrated in FIG. 23B.

In the process (s206) of determining whether the difference is within the error range, when the difference exceeds the error range, it may be determined that the position or the direction of the ultrasonic probe at the second photographing operation is different from the position or the direction of the ultrasonic probe at the first photographing operation. More specifically, the ultrasonic imaging apparatus may compute the difference between the first position and the second position in a manner such as subtraction.

In this case, the ultrasonic imaging apparatus may output a signal which induces a change in at least one of the position and the direction of the ultrasonic probe. For example, the ultrasonic imaging apparatus may output a warning message using the sound output part, the lighting part, or the displaying part, or may display at least one of a moved position and a changed direction of the ultrasonic probe using the displaying part, as illustrated in FIG. 22 (s212).

The user may move or steer the ultrasonic probe according to a screen displayed on the displaying part of the ultrasonic imaging apparatus, a sound output from the sound output part, or a predetermined color or pattern of the light output from the lighting part, such that at least one of the position and the direction of the ultrasonic probe at the second photographing operation is the same as or similar to at least one of the position and the direction of ultrasonic probe at the first photographing operation (s213).

According to the ultrasonic imaging apparatus and the method of controlling the same as described above, the three-dimensional ultrasonic volume data or ultrasonic images which are the same or similar before and after the procedure can be obtained.

According to the ultrasonic imaging apparatus and the method of controlling the same as described above, the cross-sectional images which coincide with each other can be obtained from the three-dimensional ultrasonic volume data before the procedure and the three-dimensional ultrasonic volume data after the procedure, and thus the user can compare the images before and after the procedure with respect to the same portion or adjacent portions. Therefore, the user can easily determine a result of the procedure.

According to the ultrasonic imaging apparatus and the method of controlling the same as described above, because the ultrasonic probe can be guided so as to irradiate the ultrasonic waves at a position in which the ultrasonic image is obtained before the procedure, the position of the procedure can be precisely determined, and thus the ultrasonic probe can be moved to the proper position and can irradiate the ultrasonic waves in the proper direction.

According to the ultrasonic imaging apparatus and the method of controlling the same as described above, because the ultrasonic probe can be guided so as to irradiate the ultrasonic waves at a position in which the ultrasonic image is obtained before the procedure, the position of the procedure can be precisely determined, and thus the three-dimensional ultrasonic volume data or ultrasonic images which are the same or similar before and after the procedure can be obtained.

While exemplary embodiments have been particularly shown and described above, it would be appreciated by those skilled in the art that changes may be made therein without departing from the principles and spirit of the invention, the scope of which is defined in the following claims.

What is claimed is:

1. An ultrasonic imaging apparatus comprising:
   an ultrasonic probe configured to receive a first ultrasonic signal and a second ultrasonic signal corresponding to an object;
   an image processor configured to obtain second ultrasonic volume data based on the second ultrasonic signal and relationship information between first information and second information, configured to apply the relationship information to the second ultrasonic volume data and configured to obtain a second ultrasonic cross-sectional image from the second ultrasonic volume data based on the relationship information, wherein the first information comprises a first position and a first direction corresponding to a position and a direction of the ultrasonic probe receiving the first ultrasonic signal and the second information comprises a second position and a second direction corresponding to a position and a direction of the ultrasonic probe receiving the second ultrasonic signal;

a difference obtaining part configured to obtain an error between the first position and the second position or an error between the first direction and the second direction; and a control signal generator configured to compare the error with a reference value.

2. The apparatus according to claim 1, wherein the first position and the second position are different from each other, or the first direction and the second direction are different from each other.

3. The apparatus according to claim 1, wherein the relationship information comprises a conversion by which a first cross section of first ultrasonic volume data based on the first ultrasonic signal coincides with a second cross section of the second ultrasonic volume data based on the second ultrasonic signal.

4. The apparatus according to claim 1, wherein the image processor is configured to obtain a first ultrasonic cross-sectional image from first ultrasonic volume data based on the first ultrasonic signal, and wherein at least a part of the first ultrasonic cross-sectional image overlaps with at least a part of the second ultrasonic cross-sectional image.

5. The apparatus according to claim 4, further comprising a display configured to display the first ultrasonic cross-sectional image and the second ultrasonic cross-sectional image in sequence, concurrently, or overlapped with each other.

6. The apparatus according to claim 4, wherein the image processor is configured to match at least one from among the first ultrasonic cross-sectional image and a previously obtained image with the second ultrasonic cross-sectional image.

7. The apparatus according to claim 6, wherein the previously obtained image comprises a radiographic image or a magnetic resonance image.

8. The apparatus according to claim 1, further comprising a detector configured to detect a position and a direction of the ultrasonic probe, wherein the detector comprises at least one from among an electromagnetic sensor, an optical sensor, a motion sensor, and a first communication module communicating with a second communication module installed at the ultrasonic probe.

9. The apparatus according to claim 1, further comprising an outputter configured to compute at least one from among a difference between the first position and the second position and a difference between the first direction and the second direction, and configured to output a signal which induces a change in at least one from among the position and the direction of the ultrasonic probe according to at least one from among the difference between the first position and the second position and the difference between the first direction and the second direction.

10. The apparatus according to claim 1, wherein at least one of the first ultrasonic signal and the second ultrasonic signal is an ultrasonic signal received before a procedure, and the other one is an ultrasonic signal received after the procedure.

* * * * *